United States Patent [19]

Chisholm et al.

[11] Patent Number: 5,876,945
[45] Date of Patent: Mar. 2, 1999

[54] METHODS FOR IDENTIFYING HERBICIDAL AGENTS THAT INHIBIT D1 PROTEASE

[75] Inventors: Dexter Allan Chisholm, Unionville; Bruce Aaron Diner, Chads Ford, both of Pa.; Gail K. Donaldson, Wilmington, Del.; Howard Paul Hershey, West Chester, Pa.; Douglas Brian Jordan, Wilmington, Del.; Xiao Song Tang, Hockessin, Del.; Shaojie Wang, New Castle, Del.; Jeffrey T. Trost, Wauwatsoa, Wis.; Patrick V. Warren, Philadelphia, Pa.

[73] Assignee: E. I. du Pont de Nemours and Company, Wilmington, Del.

[21] Appl. No.: 759,581

[22] Filed: Dec. 5, 1996

[51] Int. Cl.[6] ............................. G01N 33/53; C12N 9/50; C12N 9/52; C12Q 1/37
[52] U.S. Cl. ........................... 435/7.1; 435/7.72; 435/23; 435/219; 435/220; 435/221; 435/222; 435/223
[58] Field of Search .............................. 435/23, 219–223, 435/7.1, 7.72

[56] References Cited

PUBLICATIONS

Satoh, K. *Isolated and Properties of the Photosystem II Reaction Center, The Photosynthetic Reaction Center*, vol. I, pp. 289–318 (1993).

Seibert, M., Biochemical, Biophysical, and Structural Characterization of the Isolated Photosystem II Reaction Center Complex. Deisenhofer, J. and Norris, J.R., eds. *The Photosynthetic Reaction Center*, Academic Press, New York, vol. I, pp. 319–356 (1993).

Grebanier, A.E. et al., Membrane Proteins Synthesized but not processed by Isolated Maize Chloroplasts, *J. Cell Biol.*, 78, pp. 734–746 (1978).

Reisfeld et al., *Processing of a Chloroplast–Translated Membrane Protein in vivo, Analysis of the Rapidly Synthesized 32000–dalton Shield Protein and Its Precursor in Spirodela oligorrhiza*, Dept of Plant Genetics, The Weismann Institute of Science, Rehovot, Eur. J. Biochem. 124, pp. 125–129 (1982).

Minami, J.B. and Watanabe, Detection of a Precursor Polypeptide of the Rapidly–Synthesized 32,000–Dalton Thylakoid Protein in Spinach Chloroplasts, A. *Plant. Cell Physiol.* 26, pp. 839–846 (1985).

Marder, J.B. et al., Molecular Architecture of the Rapidly Metabolized 32–kilodalton Protein of Photosystem II, *J. Biol. Chem.* 259, 3900–3908 (1984).

Diner, B.A. et al., *COOH–terminal Processing of polypeptide D1 of the photosystem II reaction center of scenedesmus obiquus is necessary for the assembly of the oxygen–evolving complex.*, 263, pp. 8972–8980 (1988).

Nixon, P.J., Trost, J.T. and Diner, B.A., Role of the Carboxy 'Terminus of Polypeptide D1 in the Assembly of a Functional Water–Oxidizing Manganese Cluster in Photosystem II of the Cyanobacterium Synechocystis sp. PCC 6803: Assembly Requires a Free Carboxyl Group at C–Terminal Position 344; *Biochemistry* 31: pp. 10859–10870 (1992).

Takahashi et al., COOH–terminal residues of D1 and the 44 kDa Cpa–2 at spinach photosystem II core complex, *Febs Lett.* 06485 vol. 240, Nos. 1, 2, pp. 6–8 (1988).

Takahashi et al., *Chromatographic Purification and Determination of the Carboxy–Terminal Sequences of Photosystem II Reaction Center Proteins, D1 and D2*, Plant Cell Physiol., 31, 273–280 (1990).

Taylor, M.A. et al., *Characterization of the D1 protein in a photosystem II mutant (LF–1) of scenedesmus obliquus blocked on the oxidizing side. Evident supporting non–processing of D1 as the casue of the lesion*, Febs Letters 235: pp. 109–116 (1988).

Shestakov, S.V. et al., *Molecular Cloning and Characterization of the ctpA Gene Encoding a Carboxyl–terminal Processing Protease*, Journal of Biological Chemistry 269: pp. 1–6 (1994).

Anbudurai, P.R. et al., *The ctpA gene encodes the C–terminal processing protease for the D1 protein of the photosystem II reaction center complex*, Proceedings of the National Science, USA,, 91, pp. 8082–8086 (1994).

Fujita, S. et al., *Identification of the Carboxyl–Terminal Processing Protease for the D1 Precusor Protein of the Photosystem II Reaction Center of Spinach*, Plant Cell Physiol., 36(7), 1169–1177 (1995).

Inagaki, N. et al., *Carboxyl–terminal processing protease for the D1 precursor protein: cloning and sequening of the spnach cDNA*, Plant Molecular Biology 30 pp: 39–50 (1996).

Taguchi et al., Recognition of the Structure around the Site of Cleavage by the Carboxyl–terminal Processing Protease for D1 Precursor Protein of the Photosystem II Reaction Center, *J. Biol. Chem.*, 270(18), pp.: 10711–10716 (1995).

Packer et al., *Curr. Res. Photosynth., Proc. Int. Conf. Photosynth.*, 8th (1990), Meeting Date 1989, vol. III.13, pp. 759–762. Editor(s): Baltscheffsky, Margareta. Publisher: Kluwer, Dordrecht, Netherlands.

Magnin et al., Preliminary Steps in the Purification of the Photosystem II D1 Protein Processing Protease from Maize, *Res. Photosynth.*, Proc. Int. Congr. Photosynth., 9th (1992), vol. II, pp.: 211–214: Editor(s): Murata, N. Publisher: Kluwer, Dordrecht, Netherlands (1992).

Siber, K.R. et al., *Tsp: A tail–specific protease that selectively degrades proteins with nonpolar C termini.* Proceedings of the National Science, USA, 89: pp. 295–299 (1992).

(List continued on next page.)

*Primary Examiner*—Robert A. Wax
*Assistant Examiner*—Einar Stole

[57] ABSTRACT

D1 protease has been isolated from the alga (*Scenedesmjus obliquus*), wheat, and Synechocystis PCC 6803 and the genes encoding these enzymes have been cloned and sequenced. Native or recombinantly produced enzyme has been used to develop assays to detect herbicidal compositions capable of inhibiting the D1 protease enzyme.

14 Claims, 6 Drawing Sheets

OTHER PUBLICATIONS

Hara et al., *Cloning, Mapping, and Characterization of the Escherichia coli prc Gene, Which is Involved in C–Terminal Processing of Penicillin–Binding Protein 3,* J. Bacteriol. vol. 173, No. 15, pp. 4799–4813 (1991).

Hunt, A. P., Hussey and J. Bowyer, *The Production of Trucated Substrates for the D1 processing protease of Photosystem II,* Research in Photosynthesis, N. Murata, Editor; Kluwer Academic,Publisher, pp. 207–210 (1992).

Keiler, K.C. and Sauer, R.T., *Identification of Active Site Residues of the Tsp Protease,* Journal of Biological Chemistry, vol. 270, No. 48: pp.: 28864–28868 (1996).

Oelmuller, R. et al., *Molecular Studies of ctpA, the Carboxyl–terminal Processing Protease for the D1 Protein of the Photosystem II Reaction Center in Higher Plants,* Journal of Biological Chemistry vol. 271, No. 36, pp.: 21848–21852 (1996).

Pakrasi, H.B. et al., *Molecular Analysis of ctpA, the Carboxyl–terminal Processing Protease for the D1 protein of Photosystem II, in Higher Plants and Cyanobacteria,* Photosynthesis: from Light to Biosphere, Kluwer Academic Publishers, pp.: 719–724 (1995).

Bowyer, J.R. et al., *Carboxyl–terminal Processing of the D1 Protein and Photoactivation of Water–splitting in Photosytem II.,* Journal of Biological Chemistry, 267, pp.: 5424–5433 (1992).

Fujita, S. et al., *Cleavage of a synthetic COOH–terminal oligopeptide of D1 precursor protein by a purified processing enzyme.,* Febs Letters, 225, pp.: 1–4 (1989).

Inagaki, N., Fujita, S. and Satoh, K., *Solubilization and partial purification of a thylakoidal enzyme of spinach involved in the processing of D1 protein,* Febs Letters, 246: pp.: 218–222 (1989).

Inagaki, N., Fujita, S. and Satoh, K., *Purification and properties of a thylakoidal enzyme of spinach involved in the processing of D1 protein of PS II reaction center,* Current research in photosynthesis, M. Baltsvhffsky, Editor, Kluwer Academic Publisher: vol. III, pp.: 763–766 (1990).

Inagaki, N. et al., *Carboxyl–terminal processing protease for D1 precursor protein in spinach in Photosynthesis: from light to biosphere,* P. Mathis, Editor, Kluwer Academic Publishers: vol. III, pp.:783–786 (l995).

Keiler, K.C., Waller, P.R.H. and Sauer, R.T., *Role of a Peptide Tagging System in Degradation of Proteins Synthesized from Damaged Messenger RNA,* Science 271: pp.: 990–993 (1996).

Silber, K.R., Sauer, R.T., *Deletionof the prc (tsp) gene provides evidence for additional tail–specific proteolytic activity in Escherichia coli K–12,* Mol. Gen. Genet 242: pp.: 237–240 (1994).

Taguchi, F. et al., *Recognition signal for the C–terminal processing protease of D1 precursor protein in the photosystem II reaction center,* Febs Letters 326: pp.: 227–231 (1993).

Takahashi, Y. et al., *Genetic engineering of the processing site of D1 precursor protein of photosystem II reaction center in Chlamydomonas reinhardtii,* Plant Cell Physiology 37: pp.: 161–168 (1996).

Taylor, M.A., Parker, J.C.L. and Bowyer, J.R., *Processing of the D1 polypeptide of the photosystem II reaction center and photoactivation of a low fluorescence mutant (LF–1) of Scenedesmus obliquus,* Febs Letters 237: pp.: 229–233 (1988).

Molecular Probes (Eugene, OR 97402–0469) Product Information Sheet for Atto–Tag CBQCA, Feb. 1998.

FIG. 5

```
1                                                                    50
..........  ..........  ..........  ..........  ..........
MHSRTNCLQT  SVRAPQPHFR  PFTAVKTCRQ  RCSTTAAAAK  RDQAQEQQPW
                mature N-terminus          A
51                              ↓       ──────→             100
..........  ..........  .......VTS  EQLLFLEAWR  AVDRAYVDKS
IQVGLGLAAA  ATAVAVGLGA  AALPAQAVTS  EQLLFLEAWR  AVDRAYVDKS 101                                                                150
FNGQSWFKLR  ETY.......  ..........  ..........  ..........
FNGQSWFKLR  ETYLKKEPMD  RRAQTYDAIR  KLLAVLDDPF  TRFLEPSRLA 151                                                                200
....GTAGSV  TGVGLEITYD  GGSG......  ..........  ..........
ALRRGTAGSV  TGVGLEITYD  GGSGKDVVVL  TPAPGGPAEK  AGARAGDVIV      770 bp 201                                                                250
........GL  SLYDVSDLLQ  GEADSQVEVV  LHAPGAPSNT  R.........
TVDGTAVKGL  SLYDVSDLLQ  GEADSQVEVV  LHAPGAPSNT  RTLQLTRQKV 251                                                                300
..........  ..........  ..........  .LATFNSNTT  AAAQQAFTEL
TINPVTFTTC  SNVAAAALPP  GAAKQQLGYV  RLATFNSNTT  AAAQQAFTEL
                                                        B
301                                                       ←────
S.........  ..........  ..........  ..........  ......DIYS
SKQGVAGLVL  DIRNNGGGLF  PAGVNVARML  VDRGDLVLIA  DSQGIRDIYS LF-1 mutation
351                                           ↓                    400
ADGNSIDSAT  PLVVLVNR..  ..........  ......... .  ........LI
ADGNSIDSAT  PLVVLVNRGT  ASASEVLAGA  LKDSKRGLIA  GERTFGKGLI
                                          AS*
401                                                                450
QTVVDLSD..  ..........  ..........  .........I  GVSPDVQLDP  EVLPTDLEGV
QTVVDLSDGS  GVAVTVARYQ  TPAGVDINKI  GVSPDVQLDP  EVLPTDLEGV 451           465
CR........  ....           SEQ. ID No: 21
CRVLGSDAAP  RLFG*          SEQ. ID No: 22
```

FIG.6

```
Scenedesmus  CTG AAG GAC AGC AAG CGG GGC CTC ATA GCT GGC GAG CGC ACC TTT GGC AAG GGC CTC ATT   SEQ.ID No: 23
Wild Type    Leu Lys Asp Ser Lys Arg Gly Leu Ile Ala Gly Glu Arg Thr Phe Gly Lys Gly Leu Ile  SEQ.ID No: 24

LF-1         CTG AAG GAC AGC AAG CGG( )CC TCA TAG CTG GCG AGC GCA CCT TTG GCA AGG GCC TCA TT    SEQ.ID No: 25
Mutant       Leu Lys Asp Ser Lys Arg   Ala Ser End                                             SEQ.ID No: 26
                                    ↓
LF-1         CTG AAG GAC AGC AAG CGG( )CC TCATTA GCT GGC GAG CGC ACC TTT GGC AAG GGC CTC ATT   SEQ.ID No: 27
Revertant    Leu Lys Asp Ser Lys Arg   Ala SerLeu Ala Gly Glu Arg Thr Phe Gly Lys Gly Leu Ile  SEQ.ID No: 28
```

METHODS FOR IDENTIFYING HERBICIDAL AGENTS THAT INHIBIT D1 PROTEASE

FIELD OF INVENTION

The present invention relates to the field of molecular biology and, in particular, to a method to identify a new herbicidal target, D1 protease, necessary for the processing of the D1 protein found in the photosystem II reaction center of all higher plants. The invention further relates to methods for identifying herbicidal agents that will inhibit D1 protease, and methods and genes useful for the recombinant production of D1 protease.

BACKGROUND

The Photosystem II (PSII) reaction center contains two homologous polypeptides, D1 and D2, that are responsible for the coordination of the primary photoreactants [Satoh, K. (1993) in *The Photosynthetic Reaction Center* (Deisenhofer, J. and Norris, J. R., eds.) Vol. I, pp. 289–318, Academic Press, New York; Seibert, M. (1993) in *The Photosynthetic Reaction Center* (Deisenhofer, J. and Norris, J. R., eds.) Vol. I, pp. 319–356, Academic Press, New York]. The D1 polypeptide of PSII is present in all organisms that use oxygenic photosynthesis to fuel metabolism. The source of electrons for the electron transport chain of oxygenic photosynthetic organisms is water. The oxidation of water to molecular oxygen occurs on a tetranuclear manganese cluster that is thought to be associated with the D1 polypeptide [Nixon et al., *Biochem.* 31, 10859–10871 (1992)].

D1 is expressed in precursor form [Grebanier et al., *J. Cell Biol.*, 78, 734, (1978); Reisfeld et al., *Eur. J. Biochem.*, 124, 125, (1982); Minami, J. B. and Watanabe, A. *Plant. Cell Physiol.* 26, 839–846 (1985)], inserted into the thylakoid membrane, and processed at its C-terminus [Marder et al., *J. Biol. Chem.* 259, 3900–3908 (1984); Diner et al., *J. Biol Chem.* 263, 8972–8980 (1988); Nixon et al., *Biochem.* 31, 10859–10871 (1992)]. In cyanobacteria 16 residues are cleaved from precursor D1 (pre-D1) [Nixon et al., (1992), supra] whereas 9 residues are cleaved in higher plants (Takahashi et al., *FEBS Lett.* 240, 6–8 (1988); Takahashi et al., *Plant Cell Physiol.* 31, 273–280 (1990)), with processing occurring in all at the carboxy side of D1-Ala344. It has been suggested that this processing is effected by a protease enzyme, D1 protease.

Failure to process the carboxy-terminal extension of pre-D1 results in the inability to fully assemble the manganese cluster necessary for photosynthetic water oxidation [Diner et al., *J. Biol Chem.* 263, 8972–8980 (1988); Taylor et al., *FEBS Lett.* 235, 109–116 (1988)]. As the oxidation of water is absolutely essential to photosynthesis, prevention of this process prevents photoautotrophic growth of all cyanobacteria, algae and higher plants. Agents that inhibit the C-terminal processing of the D1 protein represent herbicidal candidates.

Although several proteins termed "D1 protease" as well as genes ostensibly encoding D1 protease enzymes have been isolated from cyanobacteria, algae, and higher plants, there is no evidence until now that these enzymes are responsible for in vivo C-terminal processing of the D1 polypeptide. For example, Shestakov et al. [*J. Biol Chem.* 269, 19354–19359 (1994)] and Anbudurai et al. [*Proc. Natl. Acad. Sci., USA* 91, 8082–8086 (1994)] teach the isolation of the ctpA gene from the cyanobacterium Synechocystis, a mutation which impairs the C-terminal processing of the pre-D1. The characterization of this gene as encoding a D1 protease was made on the basis of the impairment, measured in vivo of pre-D 1 processing in vivo and not on the basis of enzyme activity since no protein associated with this gene has as yet been isolated. Further studies by Applicants have shown, however, that the inactivation of the ctpA gene does not completely remove the ability of the mutant strain to process D1, suggesting that this protein is not wholly responsible for D1 processing.

An enzyme demonstrating D1 protease activity in vitro has been isolated from spinach [Fujita et al., *Plant Cell Physiol.* 36(7) 1169–1177 (1995)] and the gene encoding the enzyme has been cloned and sequenced [Inagaki et al., *Plant Mol. Biol.*, 30(1), 39–50 (1996)]. In vitro assays have shown that the spinach enzyme is capable of using a C-terminal fragment of the pre-D1 protein (consisting of 24 amino acids) as a substrate, but there has been no demonstration of a link between this enzyme and the in vivo processing of the pre-D1 protein [Taguchi et al., *J. Biol. Chem.*, 270(18), 10711–16 (1995)].

Pre-D1 protein processing activities have been isolated and partially purified from Scenedesmus and Pisum, [Packer et al., *Curr. Res. Photosynth., Proc. Int. Conf. Photosynth.*, 8th (1990), Meeting Date 1989, Volume 3, 759–62. Editor (s): Baltscheffsky, Margareta. Publisher: Kluwer, Dordrecht, Neth.] and from maize [Magnin et al., *Res. Photosynth., Proc. Int. Congr. Photosynth.*, 9th (1992), Volume 2, 211–14. Editor(s): Murata, Norio. Publisher: Kluwer, Dordrecht, Neth.]. These enzymes demonstrated activity in an in vitro PSII particle assay; however, no demonstration of in vivo activity of these enzymes has been obtained until now.

Isolation of an enzyme from a plant that has pre-D1 processing activity is not de facto evidence that it is indeed responsible for in vivo pre-D1 protein processing. For example, an enzyme contained in periplasmic lysates of *E. coli* tail-specific protease has been identified [Silber et al., *Proc. Natl. Acad. Sci., USA* 89, 295–299 (1992); Hara et al., *J. Bacteriol.* 173, 4799–4813 (1991)] that has about 30% identity to the putative D1 protease. Further, an enzymatic activity has been isolated by the Applicants from periplasmic isolates which has pre-D1 protein processing activity in vitro. While it is probable that these are one and the same enzyme, *E. coli* does not contain D1 and does not perform oxygenic photo-synthesis. Therefore, it cannot be concluded that an enzyme is D1 protease purely on the basis of its homology to known D1 protease-encoding genes and evidence of in vitro activity.

Thus, in order to develop a method for the screening of herbicidal agents that target D1 protease, one problem to be solved is to positively identify the enzyme that is responsible for in vivo processing of the pre-D1 protein.

Methods for assaying the presence of pre-D1 protein processing activity are known. For example, Hunt et al., [*Res. Photosynth., Proc. Int. Congr. Photosynth.*, 9th (1992), Volume 2, 207–10. Editor(s): Murata, Norio. Publisher: Kluwer, Dordrecht, Neth.] teach an assay system using a truncated peptide substrate based on the C-terminal region of the D1 protein. Similarly, Packer et al., (*Curr. Res. Photosynth., Proc. Int. Conf. Photosynth.*, supra) describe an assay using PSII thylakoid particles from the Scendedesmus D1 protease-deficient mutant LF-1. LF-1 PSII particles are incubated with a solution extracted from sonicated wildtype Scenedesmus thylakoids and D1 is processed to its normal mature size where the Mn complex is then photoligated and the photooxidation of water is detected. Finally, Taguchi et al., [*J. Biol Chem.*, 270(18), 10711–16 (1995)] teach an assay method using purified spinach D1 protease and either in vitro truncated D1 protein or synthetic oligopeptides, both containing the D1 C-terminus as a substrate. Enzyme products are identified by gel shift analysis and HPLC, respectively.

Although assay methods such as these are useful for the detection of pre-D1 processing activity, they are not readily adaptable for commercially useful high throughput screens because they use large quantities of enzyme, rely on identification of enzyme substrate by either gel or HPLC analyis, and take hours to give results. Additionally, assays using truncated D1 as substrates (Hunt et al., supra; Taguchi et al., supra) must run the assay at a pH higher than that at which the enzyme functions in vivo.

Another problem to be solved then is to develop an assay system that is facile and adaptable to high through-put screening.

SUMMARY OF THE INVENTION

The invention provides an in vitro method for identifying a herbicidal agent which inhibits D1 protease comprising: a) incubating an effective amount of a D1 protease in a sample suspected of containing a herbicidal agent with a suitable D1 enzyme substrate wherein an enzyme product is formed; and b) detecting and quantifying the enzyme product formed.

The invention further provides an in vivo method for detecting a herbicidal agent which inhibits D1 protease comprising
(a) incubating a reaction mixture containing
  (i) a wildtype cell having (A) an active D1 protease enzyme capable of processing a D1 pre-protein; and (B) a Phytosystem II core complex capable of variable fluorescence; (ii) a suspected herbicidal agent which inhibits D1 protease; and (iii) suitable growth medium for a time sufficient to permit D1 turnover; then
(b) illuminating the reaction mixture at illumination conditions of about $200\mu$ Einsteins.$m^{-2}.s^{-1}$ for a time sufficient to permit D1 turnover; and
(c) measuring variable chlorophyll fluorescence produced in step (b), whereby the level of the variable chlorophyll fluorescence is correlated with the herbicidal activity of the suspected herbicidal agent. In a further embodiment of the in vivo detection method, the reaction mixture may also contain a mutant cell containing an inactive D1 protease enzyme characterized by an inability to process a D1 pre-protein and a Phytosystem II core complex capable of variable chlorophyll fluorescence. This mutant cell is used as a control and is preferably LR-1 Scenedesmus.

It is further within the scope of the invention to provide a method for the recombinant production of D1 protease enzyme comprising: (a) transforming a suitable host cell with a vector comprising a gene encoding a D1 protease enzyme, the gene operably connected to suitable regulatory sequences; (b) growing the transformed cell under conditions wherein D1 protease is expressed; and (c) recovering the expressed D1 protease.

Finally the invention provides genes encoding D1 protease enzymes which encode the amino acid sequences of SEQ ID NOS: 4, 9, 13, and 15 wherein the amino acid sequences may encompass amino acid substitutions, deletions or additions that do not alter the function of the D1 protease.

BRIEF DESCRIPTION OF THE FIGURES, BIOLOGICAL DEPOSITS AND SEQUENCE LISTING

FIG. 5 shows a composite diagram of primer locations and amplification products used to clone and sequence the Scenedesmus D1 protease gene.

FIG. 6 shows the translated nucleotide sequence for a 60 base region of the D1 protease gene from three strains of Scenedesmus.

Figure 1:
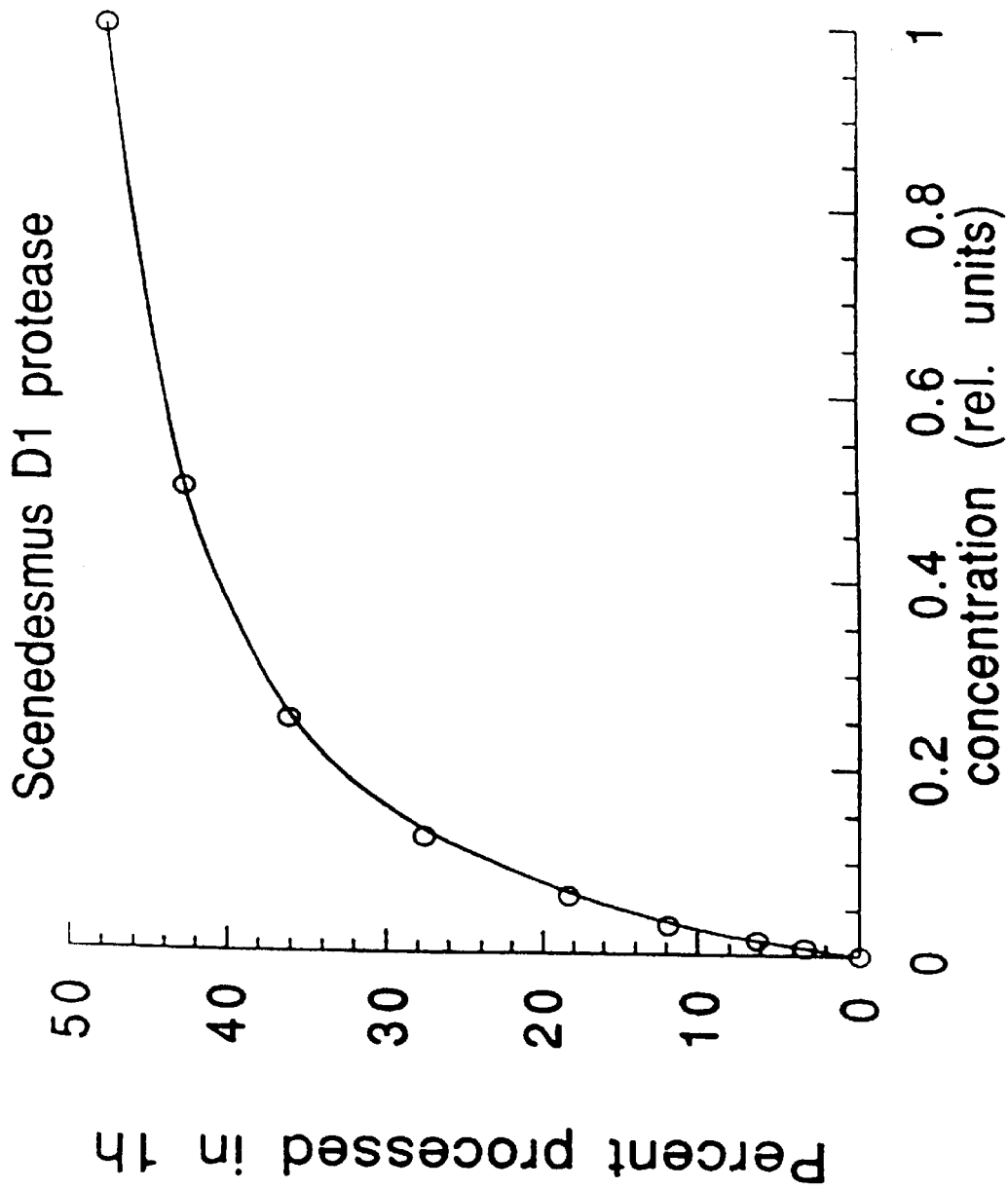
FIG. 1 is a plot of Scenedesmus D1 protease enzyme activity versus enzyme concentration.

Applicants have made the following biological deposit under the terms of the Budapest Treaty on the International Recognition of the Deposit of Micro-organisms for the Purposes of Patent Procedure:

| Depositor Identification Reference | Int'l Depository Designation | Date of Deposit |
| --- | --- | --- |
| *Escherichia coli* THSD1P containing the wheat D1 protease gene | ATCC 98186 | 26 September 1996 |

As used herein, "ATCC" refers to the American Type Culture Collection international depository located at 12301 Parklawn Drive, Rockville, Md. 20852 U.S.A. The "ATCC No." is the accession number to cultures on deposit with the ATCC.

Applicant(s) have provided 29 sequence listings in conformity with 37 C.F.R. 1.821–1.825 and Appendices A and B ("Requirements for Application Disclosures Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No. 2 to OJ EPO, 12/1992.

DETAILED DESCRIPTION OF THE INVENTION

Applicants have identified a novel herbicide target, D1 protease, and realized the use of purified D1 protease from recombinant and native sources in assay systems to identify herbicidal agents targeting D1 protease. These methods will facilitate the development of new products by the agricultural industry and have the potential for increasing the current understanding of the mechanisms by which the Phytosystem II core complex (PS II) reaction center performs its photosynthetic functions. Applicants are the first to isolate and purify a pre-D1 processing enzyme and demonstrate that the enzyme has both in vitro and in vivo functionality. Applicants have purified the D1 protease enzyme to homogeneity from the alga, *Scenedesmus obliquus*, cloned the gene on the basis of amino acid sequence, identified conserved residues that likely correspond to the active site of the enzyme, and have shown that a mutation in this gene results in the loss of in vivo D1 protease activity.

Applicants have developed an ELISA immunoassay that uses unprocessed D1 included in the thylakoid membranes or PSII core complexes isolated from the LF-1 mutant of Scenedesmus as substrates. Processing is detected by the progressive appearance of the mature C-terminus of D1 protease that is specifically recognized by an antibody. This assay is fast, automatable, allows for multiple assays to be run simultaneously, uses amounts of enzyme in the 10 femtomolar range and, in the case of thylakoid membranes, may be operated at physiological pH (i.e., about pH 4–6), similar to that found for the in vivo D1 processing system.

A method for the recombinant production of D1 protease has also been developed. Although the gene encoding spinach D1 protease has been isolated previously, to date there is no report of recombinant production of this enzyme by others.

Expression of recombinant D1 protease proceeded first by the isolation and purification of the enzyme from a suitable source, amino acid sequencing, synthesis of appropriate PCR primers based on the amino acid sequence, amplification of cDNA, cloning and isolation of the gene, and insertion of the gene into suitable expression vectors for the transformation and expression of the gene in recombinant hosts.

As used herein the following terms may be used for interpretation of the claims and specification.

"Gene" refers to a nucleic acid fragment that expresses a specific protein, including regulatory sequences preceding (5' non-coding) and following (3' non-coding) the coding region.

"Chimeric" gene refers to a gene comprising heterogeneous regulatory and coding sequences.

A "foreign" gene refers to a gene not normally found in the host organism but that is instead introduced by gene transfer techniques.

"Coding sequence" refers to a DNA sequence that codes for a specific protein and excludes the non-coding sequences.

As used herein, suitable "regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. These regulatory sequences include promoters, translation leader sequences, transcription termination sequences, and polyadenylation sequences.

"Promotor" refers to a DNA sequence in a gene, usually upstream (5') to its coding sequence, which controls the expression of the coding sequence by providing the recognition for RNA polymerase and other factors required for proper transcription. A promotor may also contain DNA sequences that are involved in the binding of protein factors which control the effectiveness of transcription initiation in response to physiological or developmental conditions.

"Constitutive promoters" refers to those promoters that direct gene expression in all tissues and at all times.

"Inducible promoters" refer to those promoters which turn on the description of a gene in the presence of an inducer.

The term "operably linked" refers to nucleic acid sequences on a single nucleic acid molecule which are associated so that the function of one is affected by the other. For example, a promoter is operably linked with a structural gene when it is capable of affecting the expression of that structural gene (i.e., that the structural gene is under the transcriptional control of the promoter).

The term "expression" refers to the production of the protein product encoded by a gene.

The terms "protein" and "polypeptide" will be used interchangeably.

The terms "D1 pre-protein", "D1 pre-polypeptide", and "pre-D1" refer to the D1 precursor protein that has been N-terminally processed but contains an additional 8 to 16 amino acid residues at the C-terminal portion of the protein which are cleaved off by D1 protease at the carboxy side of D1-Ala344 to yield the mature D1 protein.

The terms "D1 protein", "D1 polypeptide", and "mature D1 protein or polypeptide" refer to an electron transport polypeptide that is both N- and C-terminally processed and a subunit of the PSII reaction center. This polypeptide is implicated in coordinating a tetranuclear manganese (Mn) cluster which is found in the PSII reaction center of all photosynthetic organisms and is responsible for the coordination of the primary photoreactants.

The term "PSII core complex" refers to a multisubunit pigment-protein complex that consists of a PSII reaction center complex and two light-harvesting chlorophyll-proteins (CP47 and CP43).

The term "D1 protease" refers to an enzyme responsible for the processing of the D1 pre-protein at the C-terminal end for the production of the mature D1 polypeptide.

The terms "C-terminal tail" and "C-terminal tail fragment" refer to that portion of the C-terminal end of the D1 pre-protein that is cleaved off by D1 protease. The C-terminal tail fragment may comprise from about 8 to about 16 amino acid residues depending on the species from which it is isolated.

The terms "Photosystem II reaction center", "photosystem II", and "PSII" refer to a multisubunit pigment-protein complex in the thylakoid membrane in the chloroplasts of higher plants, algae, and in cyanobacteria. The Photosystem II reaction center contains the D1 polypeptide. A general review of the properties of PSII maybe found in Vermaas et al., *Cell Cult. Somatic Cell Genet. Plants* (1991), Volume 7B, 25–111. Editor(s): Bogorad, Lawrence; Vasil, Indra K. Publisher: Academic Press, San Diego, Calif.

The term "D1 turnover" refers to the degradation, biosynthesis, and reincorporation of D1 into the PSII reaction center.

The term "RACE" refers to rapid amplification of cDNA ends and describes a process used in the art of molecular biology to amplify either end of a target cDNA from a cDNA population. The RACE method is fully described in the EXAMPLES.

As used herein "Fv" means the variable fluorescence yield of chlorophyll emitted by PSII where fluorescence yield is determined by the redox state of the primary quinone electron acceptor, Qa.

The term "Fo" refers to the lower limit of variable fluorescence (Fv) when Qa is fully oxidized.

The term "Fm" refers to the upper limit of variable fluorescence (Fv) when Qa is fully reduced.

The term "Fi" refers to Fv detected by the first photons absorbed or weak light illumination following dark adaptation.

The term "weak light illumination" refers to $\leq 0.1$ photon per sec per center.

The term "Qa" will refer to the the primary quinone electron acceptor for photosystem II.

"Transformation" herein refers to the transfer of a foreign gene into the genome of a host organism or cell and its genetically stable inheritance.

The term "plasmid" or "vector" as used herein refers to an extra chromosomal element often carrying genes which are not part of the central metabolism of the cell, and usually in the form of circular double-stranded DNA molecules.

The term "restriction endonuclease" refers to an enzyme which binds and cuts within a specific nucleotide sequence within double-stranded DNA.

"Host cell" means the cell that is transformed with the introduced genetic material.

METHODS OF SCREENING FOR HERBICIDAL AGENTS

The invention provides methods of screening for compounds and agents that possess herbicidal activity by specifically interfering with the D1 protease. These assays may take a variety of formats but all rely on detecting the effective C-terminal processing of a pre-D1 or a pre-D1 fragment. The assays developed include an ELISA-based method as well as various methods adaptable for a high-throughput screen of compounds.

Assay Reagents

All assays used a variety of reagents including D1 protease, a D1 protease substrate, a primary antibody having binding affinty for the enzyme product, and an enzyme reporter conjugated to the antibody. Optionally, a secondary antibody may be used having binding affinity for the primary antibody. The enzyme reporter may be conjugated to either the secondary or primary antibody depending on the assay format.

Source of D1 protease

It is contemplated that any higher plant, algal or cyanobacterial organism that performs oxygenic photosynthesis will contain functional D1 protease to process D1 of the Photosystem II reaction center. D1 protease may be isolated from any such source for use in assay systems or to isolate genes useful for recombinant expression of the protein.

Potential sources of D1 protease include, but are not limited to, soybean, rapeseed, sunflower, cotton, corn, tobacco, alfalfa, wheat, barley, oats, sorghum, rice, cruciferous vegetables, broccoli, cauliflower, cabbage, parsnips, tomato, potato, spinach, alfalfa, sorghum, hardwood and softwood trees, forage grasses, as well as from algae, and cyanobacteria. The D1 protease will possess the ability to process the D1 pre-protein at the C-terminal end for the production of the mature D1 polypeptide. D1 protease may be isolated from natural sources or be produced recombinantly as described herein.

Preferred in the present assays is D1 protease isolated from spinach, wheat, tobacco, algae, and cyanobacteria.

Isolation And Purification Of the D1 Enzyme

The D1 protease may be isolated from plant tissue using a series of chromatographic and separation techniques useful for the purification of proteins [See, for example, Berot et al., *Proteines Veg.* (1985), 335–472 Publisher: Tech. Doc. Lavoisier, Paris, France.]

Isolated and purified spinach D1 protease is known [Fujita et al., *Plant Cell Physiol.*, 36(7), 1169–77 (1995)] from extracts of sonicated spinach thylakoids using a series of chromatographic systems including chromatography on quaternary aminoethyl anion-exchange, hydroxylapatite, copper-chelating affinity and gel-filtration columns.

D1 protease was purified from wheat, the algae Scenedesmus, and the cyobacterium Synechocystis PCC 6803 by isolating the thylakoid membranes containing the PSII reaction center and subsequent purification by Hydroxylapatite, Hydrophobic Interaction, MonoQ ion exchange, Isoelectric Focusing, and gel filtration chromatography.

Confirmation of Applicants' isolation of D1 protease was made on the basis of the demonstration of pre-D1 processing activity as determined by both in vivo and in vitro assays.

Cloning and Sequencing

N-terminal sequencing was performed on tryptic digests of purified wheat or algal protease. Methods for amino acid sequencing are known in the art [See, for example, Hunkapiller et al. (*Front. Biochem. Biophys. Stud. Proteins Membr.*, Proc. Int. Conf. (1983), Meeting Date 1982, 23–36. Editor(s): Liu, Teh-Yung. Publisher: Elsevier, New York, N.Y.) for a general review of Edman degradation, and Kasarda (U.S. Agric. Res. Serv., North Cent. Reg., Rep. (1976), ARS-NC-40, 175–80) for an example of amino acid sequencing of wheat proteins].

Amino acid sequence was used to design degenerate primers for the PCR amplification of cDNA (U.S. Pat. No. 4,683,202; U.S. Pat. No. 4,683,195). Total mRNA was extracted from the plant or algal tissue using methods well known in the art [Sambrook et al., Molecular Cloning: A Laboratory Manual, Second Edition (1989) Cold Spring Harbor Laboratory Press] and the Oligo dT-primer cDNA was synthesized. Depending on the primers used, amplification of the cDNA gave either partial or fill length PCR products from Scenedesmus and wheat as determined by gel electrophoresis. Full length cDNA amplification products were sequenced using well known base sequencing techniques [Branza-Nichita, Norica, *Stud. Cercet. Biochim.*, 38(1–2), 49–56 (1995); Cantor et al., *Mass Spectrom. Biol. Sci.* (1996), 519–33. Editor(s): Burlingame, A. L.; Carr, Steven A. Publisher: Humana, Totowa, N.J.] and inserted into suitable transformation vectors for expression.

Host cells

Suitable host cells for the recombinant production of D1 protease may be either prokaryotic or eukaryotic and the selection of a suitable host cell will be limited only by its ability to express an active enzyme. Preferred cells will be those typically useful for over-expression of foreign proteins such as *E. coli*, Bacillus, Klebsiella, fungi (e.g., Aspergillus), insects and yeasts (e.g., Pichia, Hansenula and Saccharomyces,). *E. coli* is the most preferred host.

Growth Conditions

Cells used in the present invention include preferred host bacterial cells (for recombinant expression of D1 protease) and leaves, algal cells and cyanobacteria cells (for enzyme purification and D1 protease assays).

Growth conditions for all cell types used are commonly available and well known in the art. Typically bacterial cells are grown at 30° C. in appropriate media. Preferred growth media in the present invention are common commercially prepared media such as Luria Bertani (LB) broth, or Sabouraud Dextrose (SD) broth.

Suitable media used for Scenedesmus and Synechocystis was NGY medium [Bishop, *Methods Enzymol.* 23, 372–408 (1971)] and BG11(Ripka et al., *J. Gen. Microbiol.* (1979) 111, 1–61 respectively, although any media that will support the growth and metabolism of the particular organism(s) sought to be grown will suffice.

Other defined or synthetic growth media may also be used and the appropriate medium for growth of the particular organism will be known by one of ordinary skill in the art of microbiology or fermentation science.

Suitable pH ranges for the cultures are between pH 5.0 to pH 9.0 where pH 6.0 to pH 8.0 is preferred as the initial condition.

Vectors

The present invention provides a variety of plasmids or vectors suitable for the cloning and transformation of the D1 protease enzyme into a suitable host cell. Suitable vectors will be those which are compatible with the host cell employed. Suitable vectors can be derived, for example, from a bacteria, a virus (such as bacteriophage T7 or a M-13 derived phage), a cosmid, a yeast or a plant. Protocols for obtaining and using such vectors are known to those of ordinary skill in the art [Sambrook et al., Molecular Cloning:

A Laboratory Manual—volumes 1, 2, 3 (Cold Spring Harbor Laboratory: Cold Spring Harbor, N.Y., 1989)].

Typically, the vector contains sequences directing transcription and translation of the protease gene, a selectable marker, and sequences allowing autonomous replication or chromosomal integration. Suitable vectors comprise a region 5' of the gene which harbors transcriptional initiation controls, and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions, or promoters, which are useful to drive expression of the D1 protease gene in the desired host cell are numerous and familiar to those of ordinary skill in the art. Virtually any promoter capable of driving the gene encoding the desired protein is suitable for the present invention. The T7 promoter is preferred. Termination control regions may also be derived from various genes native to the preferred hosts. Optionally, a termination site may be unnecessary, however, it is most preferred if included.

For intracellular production of the desired protein, DNA encoding the protein is linked operably through its initiation codon to the selected expression control region such that expression results in the formation of the appropriate messenger RNA. Alternatively, if production of a fusion protein is desired, DNA encoding for the desired protein is linked at its 5' end to the 3' end of the gene encoding the carrier protein. Optionally, the reverse orientation could be constructed where DNA encoding the carrier protein is linked at its 5' end to the 3' end of the DNA encoding the desired protein. Also, if desired, DNA coding for an enzyme-cleavable site may be incorporated without reading frame disruption, between the DNA encoding the desired protein and the carrier-encoding DNA, so that expression yields a fusion protein from which the desired protein can be liberated by proteolytic enzyme cleavage. An example of the fusion protein approach to protein production is provided by Contreras et al., [*Bio Technology*, 9, 378 (1991)].

Preferred within the context of the present invention are commercially available vectors such as pET-32 vector (Novagen, Madison, Wis.).

Transformation and Expression of D1 protease

Once suitable vectors are constructed they are used to transform the desired host cells. Introduction of the gene cassette containing the D1 protease gene into *E. coli* may be accomplished by known procedures such as by transformation, e.g., using calcium-permeabilized cells, electroporation, or by transfection using a recombinant phage virus [Sambrook et al., supra].

The pET-32 vector containing the D1 protease gene from wheat was used to transform *E. coli* BL21(DE3)pLysS competent cells according to standard protocols. Expression of the gene was monitored by determining the intensity of the corresponding stained band following SDS-PAGE.

Enzyme Substrates

Suitable enzyme substrates for D1 protease may be isolated from a variety of plant sources provided that D1 processing is prevented. Suitable plant sources include, but are not limited to, higher plants such as soybean, rapeseed, sunflower, cotton, corn, tobacco, alfalfa, wheat, barley, oats, sorghum, rice, cruciferous vegetables, broccoli, cauliflower, cabbage, parsnips, tomato, potato, spinach, alfalfa, sorghum, hardwood and softwood trees, forage grasses, as well as from algae and cyanobacteria. The preferred source for use in the present invention is mutant LF-1 Scenedesmus cells, possessing a mutant, non-functional D1 protease. The substrate may be purified D1 pre-protein, may be partially purified, or may be used as contained within the thyalkoid membrane or within a PSII core complex. Additionally, the substrate may be a synthetic peptide or peptide analogue (1a) containing a portion of the D1 pre-protein comprising the processing site. Alternatively, the substrate may be produced recombinantly via the expression of partial or full length genes coding for some part of the D1 polypeptide.

At least for higher plant D1 protease, the enzyme assay can be performed at physiological pH (pH 4–5) only when the thyalkoid membrane containing D1 pre-protein is used as the enzyme substrate.

Antibodies

In a preferred embodiment of the assay, antibodies were directed to a synthetic peptide comprising the final 16 residues of all known mature D1 polypeptides. The peptide was conjugated to a carrier protein and antibodies were raised in rabbits according to standard methods (see, for example, Hayes et al., *Methods Enzymol.*, 187:116–24 (1990)).

Antibodies can be either primary, having affinity for the enzyme product, or secondary, having affinity for the primary antibody, depending on the assay format.

Either primary or secondary antibodies may be linked to a reporter enzyme. A variety of reporter enzymes may be used. For example, suitable reporter enzymes include, but are not limited to, hydrolases, lyases, oxido-reductases, transferases, isomerases and ligases. Others are peroxidase, glucose oxidase, phosphatase, esterase and glycosidase. Specific examples include alkaline phosphatase, lipases, beta-galactosidase, horseradish peroxidase and porcine liver esterase. Preferred in the instant invention are alkaline phosphatase (AP) and horseradish peroxidase (HRP).

In embodiments where enzymes serve as reporters the substrate/enzyme reaction forms a product which results in a detectable signal, typically a change in color, fluorescence or chemiluninescence. In many cases chromogenic substances are an additional requirement for the color reaction. Chromogenic reagents are chosen on the basis of the reporter enzyme used. Some typical enzyme/chromogen pairs include, but are not limited to, $\beta$-galactosidase with potassium ferrocyanide or potassium ferricyanide; horseradish peroxidase with 3,3' diaminobenzidine (DAB); Glucose oxidase with NBT; and alkaline phosphotase with NBT and 5-bromo-4-chloro-3-indolylphosphate-4-toluidine (BCIP) or p-nitrophenyl-phosphate (PNPP). Methods for the use of chromatogenic substance with enzyme reactions are well known in the art and are fully described by Tijssen [Practice and Theory of Enzyme Immunoassays in Laboratory Techniques in *Biochemistry and Molecular Biology.*, eds., R. H. Burton and P. H. Van Knippenberg, (1988)].

Similarly, an example of an enzyme/substrate combination that produces a fluorescent signal is the enzyme alkaline phosphatase and the substrate Attophos [JBL Scientific Inc., San Luispo, Calif.] or HRP and N-acetyl-3,7-dihydroxyphenoxazine [Molecular Probes, Inc., Eugene, Oreg.].

An example of an enzyme/substrate combination that produces a chemiluminescent signal is the enzyme HRP and the BM Chemiluminescence ELISA Reagent substrate [Boehringer Mannheim Corp., Indianapolis, Ind.].

Preparation of an antibody-enzyme reporter conjugate may be accomplished using methods well known to those skilled in the art. Suitable examples are found in Williams [*J. Immun. Methods*, 79, 261 (1984)].

Assay Formats

In one embodiment, an ELISA format was used to assay for D1 protease. D1 protease was purified from Scenedesmus and the enzyme substrate consisted of a PSII core complex containing D1 pre-protein. Substrate cores were linked to a multi-well (96-well) microtiter plate; D1 protease was added to the wells for a fixed time period and product was analyzed by using the primary antibody (having binding affinity for the enzyme product) followed by a secondary antibody (having binding affinity for the primary antibody). The quantity of primary antibody attached to the product of the D1 protease reaction was detected through an enzyme linkage to the secondary antibody and the enzyme activity was measured calorimetrically to quantify D1 protease activity. Optionally, a primary antibody was prepared which was conjugated to an enzyme reporter, eliminating the need for the secondary antibody.

This method fits the standard ELISA immunoassay format as detailed by Omesso [Lab. 2000, 9(8), 52–6 (1995)].

In an alternate embodiment, assay methods have been developed to detect different enzyme products. For example, the action of D1 protease on the D1 pre-protein generates a mature D1 protein and a C-terminal tail fragment. Applicants have developed assay methods to detect both of these products independently.

In Applicants' assay for the detection of the mature protein, enzyme substrate was provided in the form of thylakoid membranes containing D1 pre-protein, for example, isolated from Scenedesmus LF1 mutant cells and D1 protease isolated and purified from wheat leaves. The assay was conducted in microtiter plate wells, being modified to include a permeable membrane that facilitated the separation of the enzyme reaction products. In this assay, mature D1 protein was detected using either a double (primary, secondary) antibody system or a single antibody having affinity for the mature protein and linked to an enzyme reporter.

Applicants also developed an assay to detect the C-terminal tail enzyme product. Cleavage of the C-terminal tail from the D1 pre-protein results in a free C-terminal tail having a reactive primary amine group. Various molecular probes are known which react with primary amines and may be used for peptide labeling. Examples of such molecular probes include but are not limited to fluorescamine [Stein et al., *Fluorescence News* (1973), 7(2), 9–10 (1973)]; ATTO-TAG [Molecular Probes, Inc., Eugene, Oreg.]; naphthalenedialdehyde/cyanide [Lunte et al., *Curr. Sep.*, 10(1), 19–25 (1990)]; 3-(4-carboxybenzoyl)-2-quinolinecarboxaldehyde [Liu et al., *Anal. Chem.*, 63(5), 408–12 (1991)]; isothiocyanate compounds [Stobaugh et al., U.S. Pat. No. 4,891,323); 3-Benzoyl-2-quinolinecarboxaldehyde [Beale et al., *Talanta*, 36(1–2), 321–5 (1989)]; o-phthalaldehyde [Benson et al., *Proc. Natl Acad. Sci. U.S.A.*, 72(2), 619–22 (1975)]; and ninhydrin [Udenfriend, U.S. Pat. No. 3,689,221). Preferred molecular probes within the context of the present invention are fluorescamine and ATTO-TAG.

The assay for the C-terminal tail enzyme product proceeds in a similar fashion to the assay for the mature protein, using thylakoid membranes and microtiter plates modified with the Durapore® membrane, except that the fluorescent molecular probe is reacted with the solution containing the cleaved C-terminal tail. An increase in fluorescence in this sample is an indication of D1 protease activity.

Finally, Applicants developed an assay system utilizing live algal or plant tissue for the detection of D1 protease activity. In a preferred embodiment wildtype Scenedesmus cells are used in the assay system. The wildtype cells have a normal, functional D1 protease and therefore process D1 pre-protein normally.

The assay relies on the use of chlorophyll fluorescence yield (Fv) as an indicator of the extent of pre-D1 processing. The presence of an inhibitor in the assay system blocks processing and gives rise to a higher Fv at low light intensity (Fi), and a lower Fv at high light intensity, as compared to the uninhibited wildtype used as a control.

Additionally, the assay system may be designed to incorporate the LF-1 mutant Scenedesmus (which lacks the ability to process the D1 pre-protein) as a control. In this format the wildtype and mutant cells are used together in the assay system. Mutant cells have no D1 processing ability due to a defective D1 protease and thus show a lower Fv than that of the wildtype under strong illumination [Metz et al., *Biochem. Biophys. Res. Comm.* 94, 560–566 (1980)]. Another advantage to the use of LF-1 mutants as a control is that the Fi of LF-1 cell is 2–3 fold higher than that of the wildtype cell. Thus, when wildtype cells or cells from higher plants (i.e., duck weed) are illuminated for several hours in a suitable growth medium containing D1 protease inhibitor, an increase in Fi and a decrease in Fv is seen when measured at light intensity of 10–100 photons per sec per center.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

GENERAL METHODS

Restriction enzyme digestions, phosphorylations, ligations and transformations were done as described in Sambrook, J. et al., Molecular Cloning: A Laboratory Manual, Second Edition (1989) Cold Spring Harbor Laboratory Press.

The meaning of abbreviations is as follows: "h" means hour(s), "min" means minute(s), "sec" means second(s), "d" means day(s), and "L" means liter.

Algal and Plant Strains as source of D1 Protease

The algal strains used in this study were the wildtype of *Scenedesmus oblique*, strain $D_3$, and a non-photosynthetic low-fluorescent mutant (LF-1) derived from wildtype by X-ray mutagenesis [Metz et al., *Biochem. Biophys. Res. Comm.* 94:560–566 (1980)]. A photoautotrophic suppressor strain, derived from LF-1 (LF-1-RVT-1) [Bishop, (1983) *In The Oxygen Evolving System of Photosynthesis*. (Y. Inoue et al., eds.) pp. 177–187, Academic Press, New York], was also examined. All strains were kindly provided by Norman Bishop (Oregon State University, Corvallis, Oreg.). Except where fermentors were used the cells were grown in 20 L carboys on NGY medium (Bishop, *Methods Enzymol.* 23:372–408 (1971)) in the light at 25° C.

Wheat plant tissue was obtained from wheat leaves *Triticum aestivum, var. Fidel*.

*Cyanobacterium Synechocystis* Strain PCC6803 was obtained from the Pasteur Culture Collection, Institut Pasteur, Paris, France.

Purification of D1 protease from Scenedesmus Membrane Extracts:

Membranes containing D1 protease were extracted from wildtype cells of *Scenedesmus oblique* tissue. Cells were suspended in 1 volume per weight of 20 mM HEPES-KOH, 10 mM KCl, 10% glycerol, and pH 7.25 (Buffer H) and centrifuged 5 min at 5000 rpm (4200×g) in a GS-3 rotor. The pelleted cells were resuspended in 1 volume per weight in buffer H and stored at −80° C. until use. For a typical protease isolation, 1 L of cell suspension was thawed and processed through a microfluidizer (model 110Y; Microfluidics Corporation, Newton, Mass.) by using 4 passes (18–23,000 psi) with cooling in a wet ice bath between passes. The homogenate was centrifuged 10 min at 10,000 rpm (16,000× g) in a Sorvall GSA rotor (Newtown, Conn.) to remove cell debris. The pellet was washed with buffer H to resuspend sedimented thylakoids and was added to the supernatant. The combined slurry was homogenized by stirring 30 min or by using a Teflon™/glass homogenizer. Thylakoids were collected by centrifuging 2 h (or overnight) in Beckman 45 Ti rotors at 45,000 rpm (235,000×g). The pelleted thylakoids were resuspended in buffer H by using a Teflon™/glass homogenizer and brought to a concentration of 2 mg chlorophyll/mL and 0.5% by volume TRITON X-100 from a 20% aqueous stock. After stirring for 30 min, the thylakoids were centrifuged for 2 h at 45,000 rpm (235,000×g) in a 45 Ti rotor. The TRITON X-100 supernatant was collected and stored on wet ice. The thylakoid pellet was resuspended in buffer H and brought to 2 mg/mL chlorophyll and 0.5% TRITON X-100. After stirring 30 min, it was centrifuged 2 h in a 45 Ti rotor at 45,000 rpm (235,000×g).

Hydroxylapatite Purification:

The second TRITON X-100 supernatant was combined with the first and loaded onto a 5×35 cm column of hydroxylapatite (Fast flow, Calbiochem, San Diego, Calif.) that had been previously equilibrated with 10 mM $K_2HPO_4$/$KH_2PO_4$, pH 7.0, 10% glycerol. After loading (10 mL/min), the column was washed with 500 mL of equilibration buffer and 250-mL fractions were collected. This was followed by 1 L of 100 mM $K_2HPO_4$/$KH_2PO_4$, pH 7.0 and 10% glycerol and 50-mL fractions were collected and assayed. Fractions showning D1 protease activity were concentrated and submitted to hydrophobic interaction chromatography.

Hydrophobic Interaction Purification:

The hydrophobic interaction column (TSK-Gel Phenyl-5PW, 20 mm ID×15 cm, TosoHaas) was preceded by a guard column of the same material (20 mm ID×2 cm). The column was first washed at 3 mL/min for 20–30 min with buffer B (20 mM HEPES-KOH, pH 7.25 and 20% glycerol) and then equilibrated at 10° C. with 60% Buffer A (20 mM HEPES-KOH, pH 7.25 and 20% glycerol plus 2M ($NH_4$):40% Buffer B at the same flow rate for 30–40 min. The sample was loaded onto the hydrophobic interaction column at 3 mL/min by using a Pharmacia Superloop. A linear gradient was then applied at 3 mL/min which went from 60%A:40%B to 20%A:80%B over the next 90 min. The run was completed by ramping up to 100%B over the following 20 min and maintained at that level for another 15 min. Three mL fractions were collected. Active fractions from the hydrophobic interaction column were pooled and concentrated by using a Centriprep 10 (Amicon) to 23 mL and passed through an Econo-Pac 10DG desalting column (Bio Rad, Melville, N.Y.) previously equilibrated with Buffer B and used according to the manufacturer's instructions.

Ion-Exchange purification:

The approximate 4 mL sample was then loaded onto an HR10/10 MonoQ column (Pharmacia, Pisscataway, N.J.) at a flow rate of 1 mL/min, previously equilibrated with Buffer B. The column was subsequently washed for 10 min with 100% Buffer B followed by a linear gradient from 100% Buffer B to 100% Buffer C (Buffer B plus 0.5M NaCl) over a period of 100 min and maintained at 100% Buffer C for 10 min, all at a flow rate of 1 mL/min. Two-mL fractions were collected and assayed>Active fractions were concentrated and submitted to isolectric focusing purification.

Isoelectric Focusing Purification:

Preparative isoelectric focusing was carried out in a BioRad Rotofer cell using 45 mL of 20% glycerol, 0.1% CHAPS (3-[(3-cholamidopropyl)-dimethyl ammonio]-1-propane-sulfonate), 1% Servalyte 4–6 and 0.25% Servalyte 3–10. The cell was prerun for 1 h at 12 W to establish the pH gradient and following the addition of 4 mL of sample to the center well subsequently run for 3–4 h at 5° C. at 12 W. The enzyme migrated with an isoelectric point of 5.0±0.1. The fractions were collected and assayed. Active fractions were concentrated and submitted to gel-filtration chromatography.

Gel-Filtration Purification:

The Rotofer fractions were concentrated to about 50 $\mu$L by using a Centricon™10 (Amicon) and injected onto a TSK-Gel G4000SWXL column (8 $\mu$m particle size, 7.8 mm ID×60 cm) previously equilibrated with Buffer D (BufferB plus 100 mM NaCl). The column was run at 0.25 mL/min and 0.5 mL fractions were collected. Aliquots of each fraction were diluted 1:4 or 1:6 with Buffer B and assayed. The peak of activity appeared at about 92 min from the start of the run. A comparison with the elution times of a collection of standard proteins, run under the same conditions, gave an estimated molecular mass that ranged from 36–42 kDa. This agrees favorably with a molecular mass of 42±1 kDa based on SDS-PAGE (FIG. 3) and a calculated [Genetics Computer Group (1994) In Program Manual for the Wisconsin Package, Version 8, Genetics Computer Group, Madison, Wis.] mass of 40,578 Da, based on the translated sequence of mature D1 protease (SEQ ID NO:4) from Scenedesmus.

Purification of D1 protease from wheat:

The purification of D1 protease from wheat followed essentially the same protocol as described above with the exception that the wheat chloroplasts were suspended in a hypotonic buffer (10 mM HEPES-NaOH, pH 7.3), and then the thylakoid membranes were isolated by centrifugation. The membranes were resuspended in 20 mM HEPES, 10% glycerol, pH 7.25, at 1 mg chlorophyll/mL. 0.5% TRITON X-100 was added to extract the D1 protease from the membrane.

The wheat purification differed from the above protocol at the hydroxylapatite stage where, after loading the sample onto the column, the column was first washed with 200 mL of 50 mM Pi-buffer (pH 7.0). It was then eluted with a 500 mL linear gradient from 50 to 150 mM Pi-buffer/10% glycerol (DA 7.0). The column was further washed with 150 mM Pi-buffer and the eluents were collected by fraction collector (12 mL/fraction), and each fraction was assayed for D1 protease activity.

The protocol for wheat differed from the above procedure also at the ion-exchange purification stage where the following elution protocol was used:

| Time (min) | Solvent A (20 mM HEPES/20% glyercol, pH 7.25) | Solvent B (A + 0.5 M NaCl) |
| --- | --- | --- |
| 0 | 100% | 0% |
| 10 | 100% | 0% |
| 10.01 | 80% | 20% |

-continued

| Time (min) | Solvent A (20 mM HEPES/20% glyercol, pH 7.25) | Solvent B (A + 0.5 M NaCl) |
|---|---|---|
| 40 | 80% | 20% |
| 130 | 40% | 60% |
| 130.1 | 0% | 100% |
| 140 | 0% | 100% |

Finally, the gel filtration step was expanded to include a second gel filtration where, after the first gel filtration column step (TSK-Gel, G4000SWXL), the sample was further purified using a TSK-Gel G2000SWXL column. The conditions used for this step are the same as used for the first gel filtration column.

Purification of D1 protease from Synechocystis 6803:

D1 protease was isolated from thylakoid membrane of Synechocystis 6803 in a similar manner to the protocol used for purifying wheat D1 protease described above. The thylakoid membranes were isolated from the Synechocystis cells as described in Tang et al. [*Biochemistry*, 33, 4594–4603 (1994)].

Figure 3:
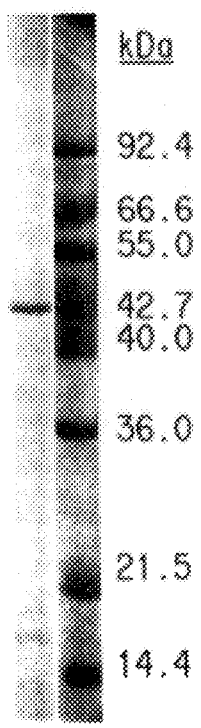
FIG. 3 is a gel showing the migration as a single band of D1 protease from Scenedesmus following the complete purification procedure.

All of the above column purification steps were performed at 4°–10° C. The yields of the various steps and their respective specific activities are listed in Tables 1–3 below. Purification to homogeneity was confirmed by a protein blot as shown in FIG. 3, where a single band identified as D1 protease is seen to migrate at 42.7 kD.

TABLE 1

SUMMARY OF THE PURIFICATION OF D1 PROTEASE FROM 500 G OF *SCENEDESMUS OBLIQUUS* CELLS

| Step | Activity (rel. units) | Protein | Specific Activity (rel. units) |
|---|---|---|---|
| Membrane extract | nd | 1 g | nd |
| Hydroxylapatite pooled fractions | 168,000 | 210 mg | 800 |
| Hydrophobic Interaction pooled fractions | 49,000 | 20 mg | 2,440 |
| MonoQ pooled fractions | 52,000 | 1.1 mg | 46,000 |
| Isoelectric Focusing pooled fractions | 15,600 | nd | nd |
| Gel filtration pooled fractions | 9,100 | 5–10 μg | $0.9$–$1.8 \times 10^6$ | nd = not determined

TABLE 2

SUMMARY OF THE PURIFICATION OF D1 PROTEASE FROM 500 G OF WHEAT LEAVES

| Step | Activity (rel. units) | Protein | Specific Activity (rel. units) |
|---|---|---|---|
| Membrane extract | nd | 2 g | nd |
| Hydroxylapatite pooled fractions | 890,000 | 130 mg | 6,846 |
| Hydrophobic interaction poole fractions | 170,400 | 12 mg | 14,200 |
| MonoQ pooled fractions | 112,000 | 500 μg | 224,000 |
| First gel filtration (TSK-Gel G4000SWXL) pooled fractions | 96,000 | 70 μg | $1.4 \times 10^6$ |
| Second gel filtration (TSK-Gel G2000SWXL) | 90,000 | 10 μg | $9.2 \times 10^6$ | nd = not determined

TABLE 3

SUMMARY OF THE PURIFICATION OF D1 PROTEASE FROM 500 G OF *CYANOBACTERIUM SYNECHOCYSTIS* CELLS

| Step | Activity (rel. units) | Protein | Specific Activity (rel. units) |
|---|---|---|---|
| Membrane extract | nd | 3.5 g | nd |
| Hydroxylapatite pooled fractions | 339,000 | 240 mg | 1,412 |
| Hydrophobic interaction pooled fractions | 53,238 | 10 mg | 5,324 |
| MonoQ pooled fractions | 42,820 | 400 μg | 107,050 |
| First gel filtration (TSK-Gel G4000SWXL) pooled fractions | 29,600 | 90 μg | $3.3 \times 10^5$ |
| Second gel filtration (TSK-Gel G2000SWXL) | 19,200 | 21 μg | $9.1 \times 10^5$ | nd = not determined

Example 1

Cloning and sequencing of the D1 protease gene from Scenedesmus

Preparation of purified enzyme for amino acid sequencing

D1 protease was biochemically isolated from Scenedesmus as described above and prepared for amino acid sequencing.

Figure 4:
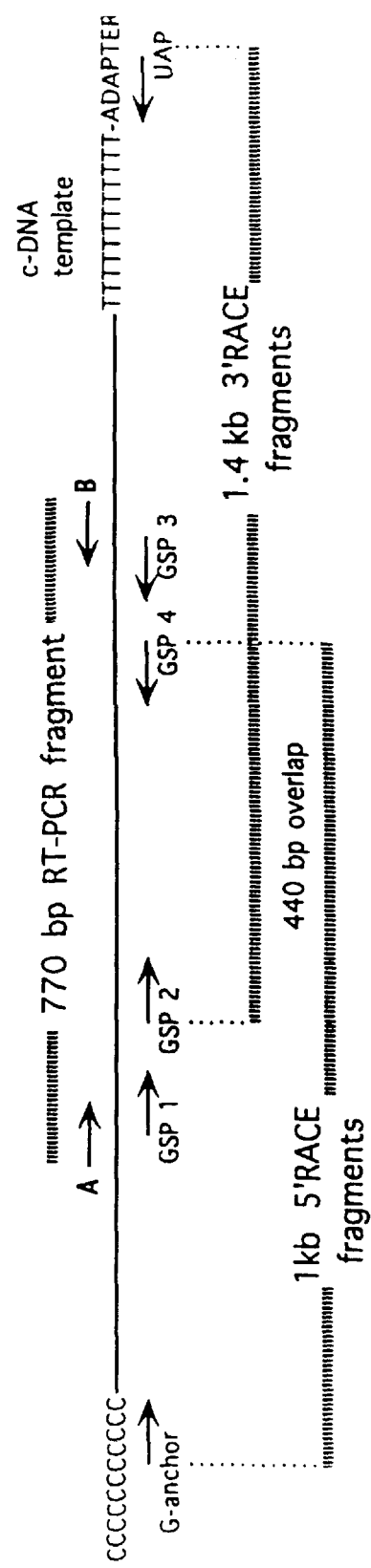
FIG. 4 shows an alignment of tryptic fragments with full length translated D1 protease gene from Scenedesmus.

SDS-PAGE and blotting were carried out according to a protocol [Best et al., (1994) In Techniques in Protein Chemistry, Vol. V, pp. 565–574, Academic Press, New York) established by the Wistar Protein Microchemistry Laboratory (Philadelphia, Pa.)]. A 12% polyacrylamide gel (30:1.8 w/w, acrylamide:bisacrylamide) 1.5 mm thick was poured, polymerized and left to stand overnight at room temperature prior to use. SDS-PAGE was run according to Best et al. [supra] with the upper buffer chamber containing 0.2% SDS and 0.1 mM thioglycolate. The solubilizing buffer (2×) contained 0.2M sucrose, 6% SDS, 125 mM Tris, 4 mM EDTA, 0.04% bromphenol blue and 2% b-mercapto-ethanol (v/v) adjusted to pH 6.9. This solution was added to an equal volume of concentrated protease solution and loaded onto the sample well of the polyacrylamide gel. The gel was run overnight at room temperature. The gel was then soaked for 25 min in Transfer Buffer composed of 10× Towbin buffer (250 mM Tris, 1.92 M glycine) +400 mL MeOH diluted to 4 L with Milli-Q water. BioRad TransBlot PVDF membrane (0.2 μm) was soaked for 10 sec in methanol and then for 20 min in Transfer Buffer. Blotting was carried out in a BioRad liquid Trans-Blot Cell using the above indicated Transfer Buffer and according to the manufacturer's instructions. A current of 240 mA was applied for 3 h at room temperature. The blot was washed three times for 5 min each with Milli-Q water and then stained for 1 min with 0.1% Amido Black in 10% acetic acid in Milli-Q water. The blot was destained for 1 min with 5% aqueous acetic acid and washed thoroughly with Milli-Q water. The blot was air-dried and sent to the Wistar Protein Microchemistry Laboratory, Philadelphia, Pa., for sequencing. Tryptic digest of the protein on the blot and subsequent HPLC purification of the tryptic fragments were performed as described in Laemmli [*Nature*, 227680–685 (1970)]. Degradative Edman sequencing was conducted at both the N-terminus and on selected HPLC purified tryptic fragments. In the latter case the MALDI (Matrix Assisted Laser Desorption Ionizaton) mass spectra were also obtained on the sequenced fragments as a confirmation of the sequence calls. The amino acid sequences obtained are shown in FIG. 4. The various tryptic fragments for which amino acid sequence data were obtained are shown aligned with the translated full-length D1 protease sequence. The mature amino terminus is noted, as is the site of the LF-1 mutation. The resultant LF-1 amino acid sequence is shown below the wildtype sequence (an asterisk denotes a stop codon). Horizontal arrows show the location of degenerate primers used to recover the initial 770 bp fragment of the gene.

Isolation of nucleic acid

Total RNA was extracted from Scenedesmus by the following procedure: 35 g of frozen cell paste was ground with 80 mL of buffer G (8M guanidine HCl, 20 mM EDTA, 20 mM MES pH 7.0 and 50 mM β-mercaptoethanol) in a PowerGen 125 tissue homogenizer (Fisher Scientific Pittsburgh, Pa.) for 60 sec set on high. The homogenate was extracted with 150 mL phenol/chloroform/isoamyl alcohol (25:24:1), and then spun in a Sorvall GSA rotor for 45 min at 8000 rpm (10,400×g) at 25° C. The supernatant was recovered and the RNA precipitated with 0.2 volumes of 1M acetic acid and 0.7 volumes of ethanol while at −20° C., overnight. The RNA was pelleted by centrifuging in a GSA rotor at 10,000 rpm (16,300×g) for 15 min at 4° C. The pellet was washed twice with 10 mL of 3M sodium acetate, pH 5.2, with a final rinse of 15 mL of 70% ethanol. The pellet was resuspended in 4 mL of RNAse-free water and stored at −70° C. until use. Poly-A containing messenger RNA was recovered from undiluted total RNA using the PolyATract system from Promega (Madison, Wis.), according to the manufacturer's instructions. The integrity of the RNA was confirmed by running on a 1% Tris-acetate agarose gel.

Total chromosomal DNA was recovered from Scenedesmus by the following procedure: about 500 mg of cells were harvested from the surface of agar plates, and resuspended in 500 μL of TSE (5 mM Tris-HCl pH 8.5, 50 mM NaCl, and 5 mM EDTA). The resuspended cells were frozen dropwise in liquid nitrogen, then ground while frozen by using a mortar and pestle. Ground cells were suspended in 1.4 mL TSE, 40 μL proteinase K (2.5 mg/mL), 100 μL 20% SDS, and 100 μL 20% Sarkosyl. The mixture was incubated at 65° C. for 2 h, then extracted with 2 mL buffer-saturated phenol, and centrifuged for 15 min at 6,000 rpm (9400×g) in a Sorvall HS-4 rotor. The supernatant was extracted with 2 mL chloroform and spun as above. The nucleic acids were precipitated from the extracted supernatant with 0.1 volume of 3M sodium acetate, and an equal volume of isopropanol. The precipitate was pelleted by spinning at 6000 rpm (9400×g) for 20 min in the HS-4 rotor, then dried, and resuspended in 900 μL TE (10 mM Tris-HCl pH 7.5, 1 mM EDTA) in microfuge tubes. RNA was digested with 20 units RNase-it (Stratagene, La Jolla, Calif.). Starches were removed by adding 300 μL of 7.8M ammonium acetate and centrifuging 30 min at 12,000×g. The DNA was precipitated by adding 1.8 mL isopropanol and centrifuging 30 min at 12,000×g. The DNA was resuspended in 1 mL TE. Typical concentrations were 400 μg/mL.

Cloning and sequencing

The HPLC purified tryptic peptides of the D1 protease were sequenced as described above and were ordered by matching them to translated D1 protease genes from wheat. Degenerate oligonucleotide primers "A" (SEQ ID NO:1) and "B" (SEQ ID NO:2) were designed to prime regions of minimum degeneracy within the peptide fragments shown in FIG. 5. Primers A and B were degenerate primers based on sequenced tryptic peptide fragments shown in FIG. 6. The resulting 770 bp RT-PCR gene fragment yielded nucleotide sequence data used to design gene specific primers GSP-1, 2,3 and 4. For 5'RACE, cDNA was oligo-dC-tailed and the first round of PCR performed with the G-anchor primer and GSP-3. The second round of PCR used the G-anchor primer and GSP-4. For 3'RACE, cDNA synthesis was primed with a special oligo-dT adapter primer which contains a region complementary to the Universal Amplification Primer (UAP). The first round of amplification was primed with UAP and GSP-1, the second round was primed with UAP and GSP-2. The spacing of the primers predicted a PCR (Polymerase Chain Reaction) product of about 770 bp.

Oligo dT-primed cDNA was prepared from Scenedesmus polyA mRNA by using a BRL SuperScript preamplification system from Gibco BRL (catalog no. 18089-011, Life Technologies, Inc., Gaithersburg, Md.). This cDNA was used as template for a PCR primed with degenerate oligonucleotides "A" and "B". The amplification employed a "touchdown" cycle sequence (Don et al., *Nucleic Acids Res.* 19, 4008 (1991)] with the annealing temperature dropping by 2 degrees every 3 cycles, from 60° C. to 50° C., followed by 15 cycles at 47° C. The reaction product was electrophoresed in a Tris-acetate low-melting point agarose gel, and a faint band of about 770 bp was excised from the gel. The gel was melted at 70° C. and a 10 μL aliquot used as template in an identical repeat amplification reaction, except that a 30 min incubation at 72° C. was included to enhance the 3' addition of single deoxyadenosines by Taq™ polymerase (Hoffinan-LaRoche, Ltd., Basel, Switzerland). This second amplification reaction produced a concentrated band of DNA that was excised from a low melt gel and ligated directly into a pGEM-T vector (Promega, Madison, Wis.), according to the supplier's instructions.

Clones containing inserts of the expected 770 bp size were sequenced on an ABI 377 automated sequencer (Applied Biosystems, Foster City, Calif.). The nucleotide sequences of the cloned fragments permitted the design of exact gene-specific primers. The primers were then used for the Rapid Amplification of cDNA Ends (RACE) in conjunction with a 5'RACE kit (Cat. No. 18373-019) and a 3'RACE kit (cat. no. 18374–025) both from Gibco BRL, and used according to the manufacturer's instructions, except for the substitution of Expand High Fidelity polymerase (Boehringer Mannheim, Indianapolis, Inn.) in place of Taq™ polymerase (Hoffman-LaRoche, Ltd.). Reaction products were run on low melt agarose gels. The 5'RACE procedure produced an amplified DNA product that was 1 kb in length. The 3'RACE procedure yielded a product that was 1.4 kb in length. Both bands were excised. As the Expand High Fidelity polymerase generates blunt-ended fragments, the following step was included to add single deoxyadenosine tails. Twenty μL aliquots of each band were incubated at 72° C. for 30 min in the presence of 10 mM Tris-HCl, pH 8.3, 50 mM KCl, 1.5 mM $MgCl_2$, 0.33 mM dATP, and 0.5 units Taq™ polymerase (Hoffman-LaRoche, Ltd.). The tailed fragments were then ligated into a pGEM-T vector.

A minimum of 4 independent clones were sequenced (both strands) for each of the 5'RACE and 3'RACE products of the LF-1 and wildtype cDNAs. Clones from the 5' end overlapped clones from the 3' end by 440 bases. Sequencing was performed as above, and the data managed using the Lasergene SeqMan program (DNASTAR Inc., Madison, Wis.). Multiple independent clones were sequenced as a precaution against mutations introduced during the course of DNA amplification. Applicants reasoned that a true mutation, present in LF-1, would appear in all LF-1 clones and none of the wildtype clones, whereas amplification mutants would appear randomly. A mutation rate of 1 error per 2000 bases sequenced was still observed despite the use of a "high fidelity" polymerase.

Once the nucleotide sequence difference between the D1 protease genes of LF-1 and wildtype was determined by sequencing the RACE clones, the mutation was verified in the Scenedesmus genome by PCR amplification and sequencing of the homologous region. Two μg each of chromosomal DNA from the wildtype, LF-1, and the suppressor strain, LF-1 RVT-1, were used as template. A pair of gene-specific primers 507 bp apart were used to prime the reaction, which used the "touchdown" cycle sequence method [Don et al., *Nucleic Acids Res.* 19(14):4008 (1991)]. The reaction products were run on a standard agarose gel, and the predominant band, running at 1200 bp, was excised. The fact that the genomic PCR product was 700 bp larger than expected indicates the presence of one of more introns. The DNA was recovered using GeneClean (Bio 101, La Jolla, Calif.), and sequenced as above using the same primers used for PCR. The sequence of the Scenedesmus D1 protease gene is given in SEQ ID NO:3 and the amino acid sequence of the encoded protein is given in SEQ ID NO:4.

Example 2

Comparison of Scenedesmus D1 protease amino acid and nucleotide sequencing and confirmation of in vivo pre-D1 processing The 5' end of the mRNA from wildtype was determined by sequencing 5'RACE clones. A total of 21 were sequenced, and the three longest showed a consistent startpoint. The remaining clones were shorter and had random startpoints, presumably the result of incomplete cDNA synthesis. The first in-frame methionine was designated the start codon.

Nucleotide sequencing of the wildtype Scenedesmus cDNA predicts a protein of 464 amino acids. Of these, the first 77 comprise a leader sequence as N-terminal amino acid sequencing of the mature protein indicated the first residue to be valine 78 (FIG. 4). A thylakoid transit sequence can be discerned with basic residues (Lys39 and Arg40), 39 and 38 residues, respectively, upstream from the mature N-terminus, followed by a region of hydrophobic residues and terminating in a typical AXA lumenal processing site [von Heijne et al., *Eur. J. Biochem.* 180, 535–545 (1989); Shackleton et al., *J. Biol Chem.* 266, 12152–12156 (1991)]. Upstream of the transit sequence is a region, enriched in serines and threonines, that is characteristic of a chloroplast signal sequence (Gavel et al., *FEBS Lett.* 261, 455–458 (1990)).

Nucleotide sequencing of the cDNA isolated from the LF-1 mutant revealed a single base deletion in the glycine 387 codon that shifts the reading frame, causing a translation stop after 2 additional amino acids (FIG. 6). The circled lysine shown in FIG. 6 is a likely component of the active site of the protease. The parentheses show the site of the single G deletion in the LF-1 and revertant strains. An arrow identifies the site of a single T insertion in the LF-1 suppressor strain, LF-1-RVT-1.

The point mutation was confirmed in genomic DNA by using PCR to directly sequence a 500 bp region of the LF-1 mutant and wildtype genomes. In addition, the same region was sequenced from an LF-1 revertant strain (LF-1-RVT-1), which was shown to have a single base-pair insertion 7 bases downstream of the LF-1 deletion. This insertion restores the proper reading frame after two amino acids that differ from wildtype (FIG. 6).

Example 3

Cloning and sequencing of the D1 protease gene from wheat

Preparation of purified enzyme for amino acid sequencing

D1 protease was biochemically isolated from wheat as described above and then prepared for amino acid sequencing. The purified enzyme was electrophoresed on SDS-PAGE according to Laemmli [(1970), supra]. The gel was stored for 24 h prior to use and 0.1 mM thioglycolate and 0.2% SDS was added to the running gel buffer. The protein was then transblotted to PVDF membrane in a BioRad Trans-Blot cell as described above and according to the manufacturer's instructions. The blot was stained with Amido Black and sent to the Wistar Microchemistry Core Facility, Philadelphia, Pa., for sequencing. The band containing the D1 protease band, was cut out of the blot. The protein band was digested with trypsin and the fragments separated on a C-18 HPLC column according to Best et al. [(1994, Techniques in Protein Chemistry V, pp. 565–574, Academic Press, New York]. Mass spectra and N-terminal sequence were performed on the cleanest and largest peptide fragments.

Isolation of Messenger RNA

Wheat leaves were harvested when plants were 15 cm tall, and 4 h after exposure to light. The leaves were cut with sterile scissors and immediately frozen in liquid nitrogen.

Total RNA was extracted from leaves by the following procedure: 35 g of crushed frozen leaves were ground with 80 mL of buffer G (8M guanidine HCl, 20 mM EDTA, 20 mM MES pH 7.0, 50 mM β-mercaptoethanol) in a Power-Gen 125 tissue homogenizer (Fisher Scientific) for 60 sec at high speed. The homogenate was extracted with 150 mL phenol/chloroform/isoamyl alcohol (25:24:1), and then spun in a Sorvall GSA rotor for 45 min at 8000 rpm at 25° C. The supernatant was recovered and the RNA precipitated with 0.2 volumes of 1M acetic acid and 0.7 volumes of ethanol while at −20° C., overnight. The precipitate was pelleted by centrifuging 10,000 rpm, 15 min at 4° C. The pellet was washed twice with 10 mL of 3M sodium acetate, pH 5.2, with a final rinse of 15 mL of 70% ethanol. The pellet was resuspended in 4 mL of RNAse-free water and stored at −70° C. until use. Poly-A containing messenger RNA was recovered from undiluted total RNA using the PolyATract system from Promega (Madison, Wis.), according to manufacturer's instructions. The integrity of the RNA was confirmed by running on a 1% Tris-acetate agarose gel.

Reverse Transcriptase PCR

Complementary DNA was prepared for use as template for PCR. To accomplish this, wheat poly-A mRNA was primed with the "reverse" primer GCNCC(GA)TCNGCCTCATA, (SEQ ID NO:29) based on the amino acid sequence data. The bases in parenthesis are the alternative bases used in the degenerate primer. Complementary DNA was synthesized with Superscript reverse transcriptase from Gibco BRL, following the manufacturer's instructions. For the first PCR, the "forward" degenerate primer was ATGGA(CT)AT(CT)TA(CT)GA(CT)GC (SEQ ID NO:5) and the "reverse" primer as shown above. Each primer concentration was 166 pMoles per 50 uL reaction. The amplification employed a "touchdown" cycle sequence (Don et al., *Nucleic Acids Res.* 19(14):4008 (1991)] with the annealing temperature dropping by 2 degrees every 3 cycles, from 60° C. to 50° C., followed by 15 cycles at 47° C. The reaction product was electrophoresed in a Tris-acetate low-melting point agarose gel, and a faint band of about 400 bp was excised from the gel. The gel was melted at 70° C. and a 10 uL aliquot was used as template for a second PCR amplification, using the above forward primer and an internally nested reverse primer, GC(TGA)AT(CT)TC(GA)AT (TGC)CC(CT)TC (SEQ ID NO:6). The second amplification reaction produced a concentrated band of about 300 bp DNA that was excised from a lowmelt gel and ligated directly into a pGEM-T vector (Promega, Madison, Wis.) according to the supplier's instructions. The resulting clone was sequenced to provide data for design of primers used for rapid amplification of c-DNA ends (RACE) and mRNA capture.

The 3' end of the gene was cloned using a capture oligo strategy as follows. The biotinylated oligo (biotin-TCTGAACCTGGAATCTCACACATCCTTGA) (SEQ ID NO:7), based on the sequence of the above PCR clone and specific to the middle of the gene, was synthesized by the DuPont oligonucleotide facility (Wilmington, Del.). The biotinylated oligonucleotide was hybridized to total mRNA and then bound to streptavidin magnetic beads (Dynal International, Oslo, Norway). The captured mRNA was used to synthesize c-DNA primed by oligo dT. After second strand synthesis, the ends were tagged with single overhanging 3'deoxyadenosine residues by incubating with Taq™ polymerase (Hoffman-LaRoche, Basel, Switzerland). The tagged DNA was then ligated into a pGEM-T vector,as above. The ligated DNA was used to transform E. coli. Transformants were selected on LB agar plates containing Ampicillin and individual colonies were screened by gel electrophoresis for plasmids containing inserts. Inserts were identified by sequencing. An 850 bp fragment of the Wheat D1 protease gene was recovered. It contains the poly-A region, the stop codon and more than half of the coding region, and overlaps the 300 bp PCR clone by about 250 bases.

The 5' end of the gene was recovered using a 5'RACE kit (Cat. No. 18373-019) from Gibco BRL, and used according to the manufacturer's instructions, except for the substitution of Expand High Fidelity polymerase (Boehringer Mannheim, Indianapolis, Inn.) in place of Taq™ polymerase.

The nucleotide sequence of the 5' and 3' clones was determined and combined to yield the complete sequence for the mature protease. The sequence of the wheat D1 protease gene is given in SEQ ID NO:8 and the amino acid sequence of the encoded protein is given in SEQ ID NO:9.

Example 4

Cloning and sequencing of the D1 protease gene from Synechocystis 6803

Preparation of purified enzyme for amino acid sequencing

D1 protease was biochemically isolated from Synechocystis 6803 as described above for Scenedesmus, Example 2, and the protein prepared for amino acid sequencing.

Cloning of the D1 protease gene ctpB

Degenerate primers were designed based on amino acid sequence data. The primers GG(TCG)GA(AG)GA(TC) TGGGT(GTC) SEQ ID NO:10 and AT(AG)TA(AGC) CCNACNAC(AG)TT(TC)TC SEQ ID NO:11 were used to generate a 600 bp PCR fragment using 25 cycles of 1 min 93° C., 1 min 55° C. and 30 sec 72° C. The fragment was ligated into a pGEM-T vector (Promega, Madison, Wis.), according to the supplier's instructions. The resulting construct was used to generate a "ctpB" gene probe for use in Southern mapping. Mapping was accomplished by digesting total Synechocystis 6803 DNA with various combinations of restriction enzymes and then separating the digested DNA by gel electrophoresis. The DNA was blotted to membranes and probed with the above construct. Analysis of the mapping data indicated that digestion of Synechocystis 6803 DNA with HindIII and Pst1 would produce a 3.2 kb fragment containing the "ctpB" gene. An enriched gene bank was created by cutting the 3.2 kb region out of HindIII-Pst1 digested DNA run on an agarose gel, and ligating the recovered DNA fragments into HindIII-Pst1 cut pBluescript vector (Stratagene, Madison, Wis.). The resulting ligation products were transformed into E. coli and plated for single colonies. Colony lifts were probed with "ctpB" gene probe to identify colonies containing the gene. Positive colonies contained the 3.2 kb HindIII-Pst1 fragment which was sequenced and found to include the entire "ctpB" gene as well as a portion of the FtsZ gene. The sequence of the Synechocystis 6803 D1 protease gene is given in SEQ ID NO:12 and the amino acid sequence of the encoded protein is given in SEQ ID NO:13.

Example 5

Isolation And Sequencing of the Gene Encoding Tobacco D1 Protease

A cDNA library was constructed from tobacco and was screened using a 770 bp fragment of the wheat D1 protease gene. Screening of the library resulted in the isolation of a 1994 bp DNA fragment. The sequence of this fragment is given in SEQ ID NO:14 and the encoded protein is given in SEQ ID NO:15. Confirmation that this sequence encodes an active D1 protease was determined by heterologous expression in E. coli and enzyme assay of the gene product.

Example 6

Transformation of E. coli with the wheat D1 protease gene and expression of active D1 protease Vector construction and Expression PolyA mRNA was isolated from wheat as described above. cDNA was synthesized by using the materials and instructions provided in the Superscript Preamplification Kit (Life Technologies, Inc., Gaithersburg, Md.). Gene specific primers were designed to prime at the 5' mature end and the 3' end of the gene. To these were added, respectively, NcoI and BamHI sites.

CAG <u>CCA TGG</u> CGC <u>TCA CGG AGG AGA AC</u> (SEQ ID NO: 16)
    NcoI           5' mature end <u>ATA CTT</u> GGG <u>ATC CAT</u> ATC ACG (SEQ ID NO: 17)
  Stop       BamHI The "touchdown" PCR program (see above) consisted of 1 min at 94° C., an annealing step of 1 min, and then 1 min at 72° C. The temperature of the annealing step was progressively lowered starting at 60° C. for 1 min (for 3 cycles) and then lowered by 2 degrees every three cycles until 50° C. was reached whereupon 5 cycles were performed. The PCR product was cut with the restriction enzymes, NcoI and BamHI, from Promega (Madison, Wis.). This fragment was then subcloned into a pET expression vector (pET-32a(+) (Novagen Inc., Madison, Wis.) that encodes the protease fused to thioredoxin, and a linker containing an enterokinase proteolytic cleavage site. The expression vector was transformed into the E. coli non-expression host strain, NovaBlue (Novagen, Madison, Wis.) to obtain high plasmid yields. The transformed cells were plated out on LB agar. Ten colonies were selected and grown up in LB broth containing ampicillin (100 µ/mL) at 37° C. The plasmid was purified according to the method described in the Wizard planned purification system (Promega, Madison, Wis.). The gene was sequenced in all ten plasmids to confirm the gene sequence and to check for the absence of PCR errors. The correct construct was then used to transform the tightly regulated E. Coli host expression strain (BL21(DE3)pLysS) where expression is under the control of a T7 promotor. The transformed cells were grown at 37° C. to an optical density of 0.4 OD at 600 nm in LB broth and then induced with IPTG (1 mM) for three h. Transformed cells have now been grown in volumes as large as a 101 fermentor. Induction with IPTG produced inclusion bodies that amounted to ~15% of the total cell protein and which were about 75% enriched in D1 protease.

Purification and Enzyme activity:

After induction, the cells were harvested by centrifugation and resuspended in 20 mM HEPES-NaOH buffer, pH 7.3, containing 0.1% TRITON X-100, 0.1 mg/mL lysozyme, 5 mM $MgCl_2$, 0.01 mg/mL RNAse and 0.05 mg/mL DNAse at room temperature. The suspension was spun down and the supernatant discarded. The pellet was resuspended in 20 mM HEPES-NaOH, pH 7.3, 1 mM EDTA, 0.1% TRITON X-100 and 0.3M NaCl. The suspension was again spun down and the supernatant discarded. The pellet (90% enriched in the thioredoxin-D1 protease fusion) was resuspended in 20 mM HEPES-NaOH, pH 7.3, 1 mM EDTA and 5 mM DTT. All centrifugation steps were for 15 min at 12,000 rpm.

The pellets were solubilized in 8M guanidinium hydrochloride, 5 mM EDTA in 20 mM HEPES-NaOH, pH 7.3 at 1 mg protein/mL. The protein was refolded by 1:100 dilution into 20 mM MES, pH 6.0, 20 mM CHAPS, 10% glycerol, 1 mM reduced glutathione, 1 mM oxidized glutathione. The concentrated protein was added either dropwise or with a peristaltic pump at a rate of 10 mL in 30–40 min to 1 liter of five additions were made with a one h interval between each addition for a total of 50 mg protein. The solution was then incubated overnight at 4° C. The protein was then concentrated at 4° C. using a YM30 membrane in an Amicon concentration cell. The concentrated protein was then loaded onto a MonoQ (HR10/10, Pharmacia,) column equilibrated with 15 mM CHAPS (3-[(3-cholamidopropyl)-dimethyl-ammonio]-1-propane sulfonate), 10% glycerol and 20 mM HEPES-NaOH, pH 7.3. The protein was eluted using a NaCl gradient from 0–400 mM in the same buffer. The fractions containing purified protease were then concentrated and further purified to homogeneity on a TSK4000 (G4000SW, 21.5×600 mm, TosoHaas) column with 15 mM CHAPS, 10% glycerol and 20 mM HEPES-NaOH, pH 7.3 as elution buffer. Cleavage of the N-terminal tags with enterokinase produces mature D1 protease with only three additional residues at its N-terminus. N-terminal cleavage increases about five-fold the specific activity of the protease.

The enzymatic activity of the recombinant enzyme was assayed by using the microtiter plate ELISA assay with PSII core complexes from Scenedesmus LF-1 as substrate. The specific activity of the recombinant enzyme, expressed in relative units, is close to that of the natural enzyme isolated from wheat leaves.

Example 7

Synthesis of chloromethyl ketone inhibitors as potential D1 protease inhibitors.

A variety of chloromethyl ketones were synthesized as potential D1 protease inhibitors.

Abbreviations used in the following discussion of synthesis are listed below.
LRMS: Low Resolution Mass Spectrometry
HRMS: High Resolution Mass Spectrometry
FAB: fast atom bombardment
CI: chemical ionization
Ala: L-alanine
Leu: L-leucine
Asp: L-aspartatic acid
Boc: t-butoxycarbonyl
Bzl: benzyl
Z: benzyloxycarbonyl
DCC: dicyclohexylcarbodiimide
Su: succinimidyl
THF: tetrahydrofuran
DMF: dimethyl formaide Preparation of Boc-Ala-$CH_2$Cl A. Generation of diazomethane In a 500 mL round bottom flask, connected with a 500 mL addition funnel, containing potassium hydroxide (12 g) in water (20 mL) was added diethyl ether (40 mL) and diethyleneglycol monoethyl ether (100 mL), then heated to 70° C. (oil bath). Diazald® (43 g) (Aldrich Chemical Co., Milwaukee, Wis.) in 400 mL of diethyl ether was poured into the addition funnel. As the diethyl ether started to distill, the Diazald® solution was added dropwise over a 30 min period. Ethanol (100 mL) was added to the addition funnel until the distillate became colorless.

B. Preparation of Boc-Ala-$CH_2N_2$

Boc-Ala-OH (24.6, 130 mmol) was dissolved in THF (45 mL) and cooled to –20° C. The carboxyl group was activated by adding N-methylmorpholine (14.3 mL) and isobutyl chloroformate (17.0 mL) for 5–10 min. The resulting salt was filtered off and washed with 40 mL of cold THF. The freshly generated diazomethane was poured slowly into the filtrate at 0° C. The resulting mixture was warmed to room temperate after the nitrogen evolution finished. After 1 h stirring at room temp, the solvent was removed by rotavap to give Boc-Ala-$CH_2N_2$ as bright solid of 28.9 g.

C. Synthesis of Boc-Ala-$CH_2$Cl

To the crude Boc-Ala-$CH_2N_2$ (28.9 g) in diethyl ether (200 mL) was added 5.0N HCl in dioxane (1 equiv., 28.5 mL) dropwise at 0° C. The solution turned colorless upon addition completion. The resulting solution was washed with cold water (200 mL), sat NaCl (aq) (150 mL×2), dried over $Na_2SO_4$. After filtration, the filtrate was concentrated to give crude product of 25.6 g. The crude solid was purified by flash silica gel column chromatography (20% hexane in ethyl acetate) and yielded pure Boc-Ala-$CH_2$Cl of 20 g.

LRMS(CI): m/e calculated for M ($C_9H_{16}ClNO_3$)+H: 222. Found: 222.

Preparation of H-Asp(OtBu)-Leu-OH

Z-Asp(OtBu)-OH (10.23 g) in THF (50 mL) was added N-methyl-morpholine (3.30 mL) and isobutyl chloroformate (3.90 mL) at –20° C. After 10 min, the reaction mixture was added to the solution of H-Leu-OBzl (11.81 g in 50 mL $HCl_3$) at –20° C., followed by addition of triethylamine (4.18 mL). The resulting mixture was allowed to warm to room temp. After filtering off the salt, the filtrate was concentrated to an oil. The oil was dissolved in 100 mL of ethyl acetate; washed with 0.2N HCl, 5% $NaHCO_3$ and sat. NaCl; dried over $Na_2SO_4$. After filtration, the solvent was evaporated to give Z-Asp(OtBu)-Leu-OBzl as an oil of 14.81 g.

The Z-Asp(OtBu)-Leu-OBzl (15.6 g) in methanol (50 mL) was added 10% Pd on carbon (0.17 g) and was hydrogenated on a Paar Shaker. After filtering off the catalyst, the filtrate was concentrated to give a foamy solid. The crude product was triturated with diethyl ether to yield 8.03 g of H-Asp(OtBu)-Leu-OH.

LRMS(CI): m/e calculated for M ($C_{14}H_{26}N_2O_5$)+H: 303. Found: 303.

Preparation of Z-Leu-Asp(OtBu)-Leu-OH

Z-Leu-OH (15.92 g) and N-hydroxysuccinimide (6.9 g) were dissolved in dioxane and cooled to 0° C. To the cooled solution, DCC was added and stirred at 0° C. for 0.5 h, then room temp overnight. After filtering off the byproduct urea, the filtrate was concentrated to give crude Z-Leu-OSu as an oil.

The H-Asp(OtBu)-Leu-OH (3.02 g), sodium bicarbonate (1.68 g), and 30 mL of water were mixed to give a mixture of pH 8. Z-Leu-OSu (3.63 g) in dioxane (30 mL) was added to the mixture and was stirred at room temp for 2 h. The reaction mixture was acidified by addition of conc. HCl to pH 1.0, then was extracted with ethyl acetate (30 mL×3). The combined extracts were dried over $Na_2SO_4$, filtered, and concentrated. The crude product was dissolved in methanol and chromatographed on a column of Sephadex™ LH20 to yield Z-Leu-Asp(OtBu)-Leu-OH as a foamy solid (4.43 g).

LRMS(CI): m/e calculated for M ($C_{28}H_{43}N_3O_8$)+H: 550. Found: 550.

Preparation of Z-Leu-Asp(OtBu)-Leu-Ala-$CH_2Cl$

Boc-Ala-$CH_2Cl$ (2 g) in 5 equiv of HCl in dioxane was stirred at room temp for 1 h. After removal of solvent, the residue was triturated with diethyl ether to give crude H-Ala-$CH_2Cl$ (1.41 g). The Z-Leu-Asp(OtBu)-Leu-OH (2.68 g) and N-methylmorpholine (0.54 mL) were dissolved in THF (25 mL), the cooled to −20° C. Isobutyl chloroformate (0.64 mL) was added to generate the mixed anhydride, which was transferred to the H-Ala-$CH_2Cl$ (1.41 g in 10 mL of DMF) solution at −20° C. The resulting mixture was allowed to come to room temp and reaction was completed in 3 h. The salt was removed by filtration. The filtrate was concentrated, redissolved in ethyl acetate (100 mL). The solution was washed with 0.2N HCl, 5% $NaHCO_3$, sat. NaCl; dried over $Na_2SO_4$, filtered, and concentrated to yield crude solid of 3.19 g. The crude Z-Leu-Asp(OtBu)-Leu-Ala-$CH_2Cl$ was purified by Sephadex LH20 column chromatography.

LRMS(FAB): m/e calculated for M ($C_{32}H_{49}O_8N_4Cl$)+H: 653. Found: 653.

HRMS(FAB): m/e calculated for [M+H]: 653.3317. Found: 653.3283

Preparation of Z-Leu-Asp-Leu-Ala-$CH_2Cl$

The Z-Leu-Asp(OtBu)-Leu-Ala-$CH_2Cl$ (0.653 g) in methylene chloride (5 mL) was stirred with trifluoroacetic acid (5 mL) at room temp for 2 h. After removal of the volatile species, the residue was triturated with diethyl ether to yield Z-Leu-Asp-Leu-Ala-$CH_2Cl$ as white powder (0.47 g).

LRMS(FAB): m/e calculated for M ($C_{28}H_{41}ClN_4O8$)+H: 597. Found: 597.

HRMS(FAB): m/e calculated 597.2691 for [M+H]. Found: 597.2678.

Example 8

Microtiter plate assay of D1 Protease

Preparation of primary antibody

A synthetic peptide (EVMHERNAHNFPLDLA (SEQ ID NO:18)) identical to the final 16 residues of practically all known sequences of polypeptide D1 [Satoh, (1993) in *The Photosynthetic Reaction Center* (Deisenhofer, J. and Norris, J. R., eds.) Vol. I, pp. 289–318, Academic Press, New York], was synthesized (>95% pure) and coupled to keyhole limpet hemocyanin (KLH) by using glutaraldehyde (Multiple Peptide Systems) at a 1:1 ratio of peptide to KLH (w/w). New Zealand rabbits were immunized using the peptide-KLH conjugate suspended in PBS buffer (3.1 mg/mL) and emulsified by mixing with an equal volume of Freund's Adjuvant and injected into 5–6 subcutaneous dorsal sites for a total volume of 0.6 mL. The initial immunization was followed by three booster injections 21 d apart. The antiserum that was used as primary antibody in the assays was obtained from one rabbit 10 d after the second booster injection. The animals were bled from the ear vein, the blood heated at 37° C. for 1 h, chilled to 0° C. for 15 h and centrifuged. Further purification of the supernatant was not attempted. The serum was frozen and stored at −80° C.

Preparation of Microtiter Plates

PSII core complexes were isolated from Scenedesmus wildtype and LF-1 as described by Diner et al., [*J. Biol Chem.*, 263, 8972–8980 (1988)] and stored at −80° C. Immediately before use, they were diluted to 2 ng Chl/μL using TBS (20 mM Tris-HCl, pH 8.0, 150 mM NaCl). Each plate requires 5 μg Chl or 2.5 mL of diluted LF-1 cores and 0.2 μg Chl or 100 μL of WT cores. Ten plates were typically prepared at the same time.

Glutaraldehyde (25% solution, EM grade, Electron Microscopy Sciences, Fort Washington, Pa.) was freshly opened from sealed ampoules and was diluted to 0.5% with TBS immediately before use (2.4 mL per plate). Twenty-five μL of the diluted glutaraldehyde were pipetted, using a Costar octapipette, into each well of a 96-well microtiter plate (Nunc Immunoplate Maxisorp, Cat. no. 439454). Twenty-five μL of the diluted LF-1 cores were pipetted per well into all but 3 wells of the plate (in column 12) and the plate shaken to mix the glutaraldehyde and the core complexes. Twenty-five μL of the diluted WT cores were pipetted per well into the remaining 3 wells and the plate again well-shaken to mix the glutaraldehyde and the core complexes. The plates were allowed to stand at room temperature for 1–2 h with continuous shaking at room temperature. The wells of column 12 are not incubated with protease and thereby show the maximum (WT wells) and minimum (LF-1 wells) signals attainable with the D1 protease assay.

At the end of the incubation period, the wells were washed to remove unbound cores and blocked to prevent non-specific protein binding. Both were accomplished by giving each well 3 rinses with TTBS (50 mM Tris-HCl, pH 7.4, 150 mM NaCl, 0.2% Tween 20) and then filling each well with TTBS. The plates were then incubated for 1–2 h at room temperature, after which the wells were again rinsed. The remaining TTBS was aspirated and shaken out of the wells. The plates were then sealed in plastic bags containing a moistened paper towel. The plates were then stored in a −20° C. freezer and could be used over a period of months. It has been observed, however, that the background signal observed in blank wells lacking enzyme gradually increased with storage time.

Assay of Enzyme Activity

The samples to be assayed were diluted to 50 μL with 20 mM HEPES-KOH, pH 7.25, 20% glycerol (assay buffer) and placed in individual assay wells. Usually only rows B–G and columns 2–11 were used for assaying enzyme activity because the wells at the periphery of the plate often gave slightly higher signals. The wells containing the control WT and LF-1 cores in column 12 were also left empty. The samples of D1 protease were typically allowed to incubate for 1 h at room temperature after which each well was given 3 quick rinses with TTBS and then allowed to soak for 2 min. The TTBS was aspirated off and then refilled for another 2 min incubation. This was repeated two more times. The plate was then aspirated dry and turned over to tap any remaining buffer onto a paper towel.

Five µL of primary antibody serum, directed against the final 16 residues of mature D1 polypeptide (Multiple Peptide Systems, see below), was diluted with 5 mL of PBS (1.44 g $Na_2HPO_4$, 0.24 g $KH_2PO_4$, pH 7.2, 8 g NaCl, 0.2 g KCl and 20 g bovine serum albumin per liter), previously filter sterilized through a 0.2 µm membrane. Fifty microliters of diluted secondary antibody solution were added to each well and the covered plates allowed to incubate on a rotary shaker at 37° C. After 30 min, the plate was washed as above with the 3 cycles of soak and aspiration using TTBS.

Ten µL of goat anti-rabbit conjugated to alkaline phosphatase (Sigma Immunochemicals A-7539) were diluted into 5 mL of TBS (3 g Tris-HCl, pH 8.0, 8 g NaCl, 0.2 g KCl and 20 g bovine serum albumin per liter) previously filter sterilized through a 0.2 µm membrane. Fifty microliters of diluted primary antibody solution were added to each well and the covered plates were allowed to incubate on a rotary shaker at 37° C. After 30 min, the plate was washed as above with the 4 cycles of soak and aspiration using TTBS.

The colorimetric substrate consisted of one 5 mg tablet of p-nitrophenyl phosphate (Kirkegaard & Perry Laboratories, 50-80-01) dissolved in 5 mL of 5× diluted DEA Buffer (Kirkegaard & Perry Laboratories, Gaithersburg, Md., 50-80-02). Fifty microliters of this solution were added to each well and the plate incubated at 37° C. in a microtiter plate reader (Molecular Devices, Thermomax) interfaced to a Macintosh SE/30. The time course of the increase in the concentration of p-nitrophenol was typically determined by monitoring the increase in absorption at 405 minus 650 nm for 10 min. Activity is expressed in terms of mOD/min. Alternatively, the plates were incubated at 37° C. for 1 h and measured by the same wavelength difference after quenching the reaction with 50 µL per of 3M NaOH. The extent of cleavage of the D1 polypeptide in the test well could be determined by comparison with the control LF-1 and WT wells that had not been incubated with enzyme. The ratio of the signals from these wells were usually 1:15–30, respectively, indicating that the primary antibody directed against the mature C-terminus has a much reduced affinity for the preprocessed C-terminus of the D1 polypeptide.

An example of the dependence of the assay on enzyme concentration is shown in FIG. 1 where the intensity of the color reaction is shown to be proportional to enzyme concentration up to approximately 20% of pre-D1 cleaved.

FIG. 1 is a plot of Scenedesmus D1 protease enzyme activity versus enzyme concentration. Purified enzyme was diluted with assay buffer (20 mM HEPES-KOH, pH 7.25, 20% glycerol) at the indicated relative concentrations and incubated in the microtiter plate wells for 1 h at room temperature. The most concentrated enzyme solution used was approximately 13 nM. At 50 µL/well this is equivalent to 650 fmoles enzyme/well. The ordinate is expressed as the percentage of the signal obtained with a concentration of wildtype PSII cores equal to those of LF-1. One hundred percent corresponds to fully processed cores.

Figure 2:
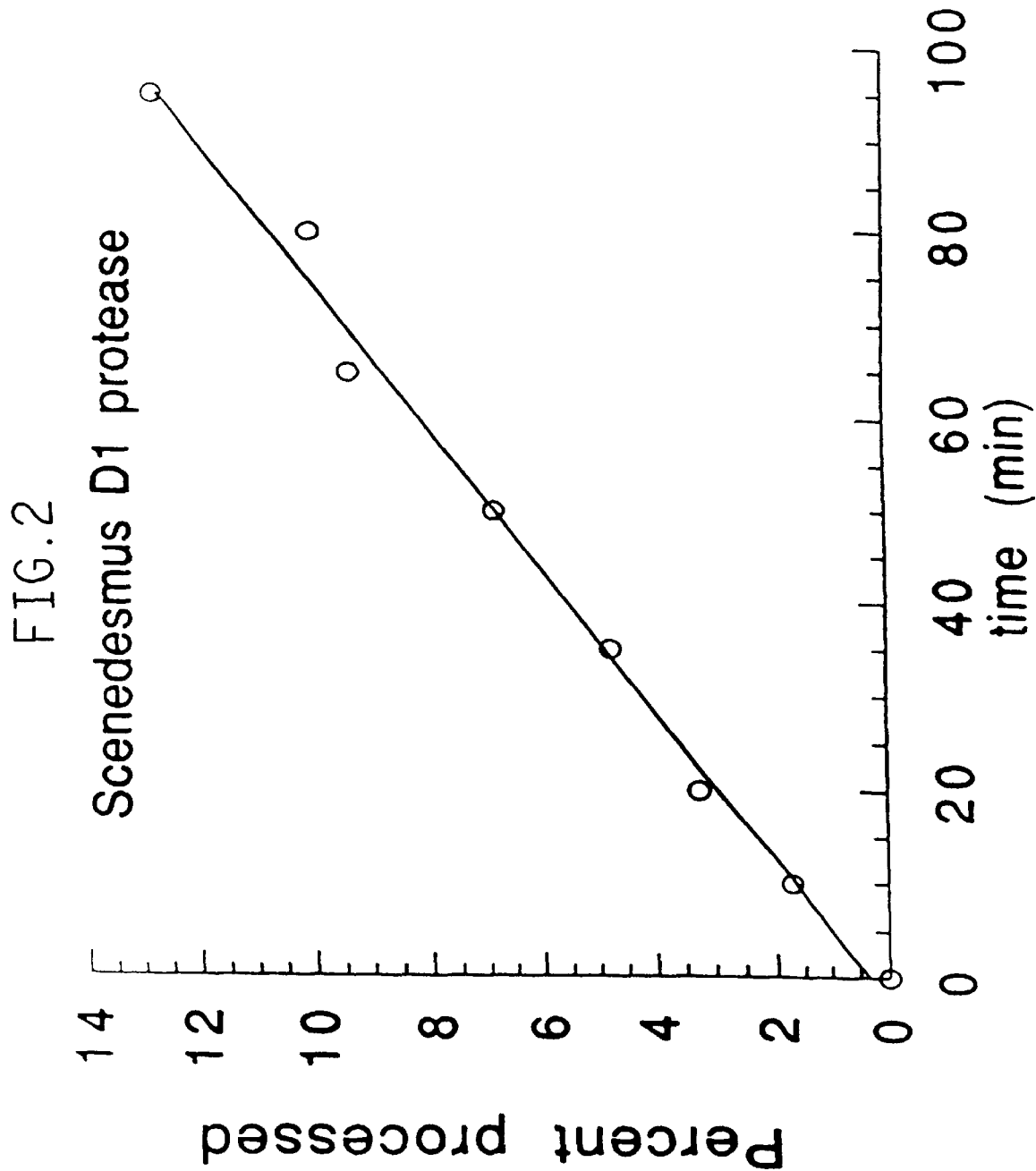
FIG. 2 is a plot of a time course of a D1 protease assay.

As shown in FIG. 2, the assay is also linear with time up to approximately the same percentage of cleaved pre-D1. The optimum pH is 6.3±0.3.

As shown in FIG. 2, purified enzyme was diluted to a concentration of 810 pM or 40 fmoles per well (50 µL) with assay buffer. The enzyme incubated was in the microtiter plate wells at room temperature for the indicated times. The ordinate is expressed as the percentage of the signal obtained with a concentration of wildtype PSII cores equal to those of LF-1. One hundred percent corresponds to fully processed cores.

Example 9

In vitro high-throughput screening assay using thylakoid membrane fragments containing pre-D1 and wheat D1 protease Example 9 demonstrates an in vitro assay for D1 protease. The assay resulted in the generation of 2 different enzyme products consisting of a mature D1 protein and a C-terminal tail portion of the pre-protein. The assay was capable of detecting both type of products. Because this assay used isolated thylakoid membrane containing the D1 pre-protein substrate the assay could be run at a pH similar to that found in the whole plant.

DETECTING THE MATURE D1 ENZYME PRODUCT
Source of Substrate and D1 Protease

The PSII-enriched thylakoid membrane fragment was isolated from Scenedesmus LF-1 mutant cells using a mild TRITON X-100-treatment as follows:

Scenedesmus cells were broken in a "bead-beater" (Biospec Products, Bartlesville, Okla.) in an ice-water bath with 1-mm diameter glass beads using 10 bursts of 45 sec each. The thylakoid membranes were separated from the homogenate using centrifugation, and then the PSII-enriched thylakoid membrane fragment was isolated using TRITON X-100-treatment (TRITON:chlorophyll=15–20: 1) and centrifugation according to the procedure described by Miyao et al., [(1991) *Biochim. Biophys.* Acta 1056, 47–56]. The thylakoid membrane fragments contain the unprocessed D1 polypeptide.

Wheat D1-protease was purified from wheat leaves as described in the
GENERAL METHODS
Preparation of Assay Plates The assay made use of a 96-well format multiscreen assay system made by Millipore Corporation (Bedford, Mass., OF1730; cat No. MADV NOB). Each well of the 96-well microtiter plate contained a low-protein-binding Durapore membrane (pore size=0.65 mm). Wells were pre-wet with TBSM (TBS buffer plus 5 mM $MgCl_2$), and then the TBSM solution was removed by drawing the liquid through the membrane using the MultiScreen assay system with its vacuum manifold and pump, according to the manufacturer's instructions. All washes and rinses were performed in a similar manner. Wells were then blocked with the blocking reagent for 5 min as recommended by the manufacturer and the blocking solution was removed by applying vacuum.
Enzyme assay and signal detection A 20–50 µL reaction mixture was added to each well consisting of LF-1 thylakoid membrane, (final PSII reaction center concentration to 0.25 mM) and wheat D1-protease (final enzyme concentration:200 pM) in reaction buffer (20 mM Mes-NaOH, pH 5.2, 5 mM $MgCl_2$ and 5 mM $MnCl_2$). Plates were incubated for 15 min at room temperature with shaking at which time the reaction liquid was removed and the plate was washed once with TBSM. At this stage, only the thylakoid membrane was left in the well because of the presence of $MgCl_2$. The thylakoid membrane will stack together (as in vivo), and the stacked thylakoid membranes are too large to pass through the plate membrane pore.

Two types of primary antibodies were used. Type 1 was a primary antibody prepared as described in Example 8, containing no reporter. Type 2 affinity purified primary antibody was conjugated to the reporting enzyme Horseradish peroxidase (HRP)(Sigma Chemical Co., St. Louis, Mo.) Both type 1 and type 2 antibodies recognized the mature D1 C-terminus.

Either type 1 or type 2 primary antibody was added into each well, and plates were incubated at 37° C. for 10 min. In assays using type 1 antibody, anti-rabbit IgG alkaline phosphatase conjugate was added to each well and plates were allowed to incubate again at 37° C. for additional 20 min. After this, incubation plates were washed with TBSM to remove the unbound antibodies. When using type 2 antibody for the assay, no secondary antibody was added, and the plate was directly washed after primary antibody incubation.

When using the unlabeled type 1 primary antibody, plus secondary antibody, 50 uL of the calorimetric substrate, p-nitrophenyl phosphate, or fluorescent substrate, Atto-phos (JBL Scientific Inc., San Luispo, Calif.), was added to each well, and plates were incubated for 10–30 min. During the transfer process, the substrate (p-nitrophenyl phosphate or Atto-phos) was separated from the alkaline phosphatase, stopping the reaction automatically.

When using the type 2 HRP conjugated primary antibody 50 mL of calorimetric substrate, TMB (Kirkgaard & Perry Laboratories, Inc., Gaithersburg, Md.) or fluorescent substrate, N-acetyl-3,7-dihydroxyphenoxazine (A6550, Molecular Probes, Inc., Eugene, Oreg.) or chemiluminescence substrate, BM Chemiluminescence ELISA Reagent (13oehringer Mannheim Corp., Indianapolis, Inn.) was added to each well. Plates were incubated for 15 min. Next the substrate was transfered to a regular plastic 96-well microtiter plate using the manifold and vacuum and then read for absorption or fluorescence or chmiluminescence intensity. In the case of fluorescence and chemiluminescence detection, the signal can be directly detected without a filtration step. Measurements can be made in end point or kinetic mode.

Finally, plates were read on a microtiter plate reader, measuring the change in fluorescence or absorption. Control wells included all the same reagents as the experimental with the exception of D1 protease enzyme.

TABLE 4

|  | Without D1P | With D1P |
| --- | --- | --- |
| Type1 AB and PNP (Absorbance OD 450-650) | 0.06 OD | 0.365 OD |
| Type1 AB and ATTOPHOS (Fluorescence intensity) | 414 RU | 1070 RU |
| Type2 AB and TMB (Absorbance at OD 650450) | 0.023 OD | 0.141 OD |
| Type2 AB and TMB and 7 mM of Z-LDLA-CMK*, ++ (Absorption change) | 0.023 OD | 0.081 OD |
| Type 2 AB and A6550 (Fluorescence intensity) | 134 RU | 263 RU |
| Type2 AB and BM (Chemiluminescence intensity) | 16 RU | 33 RU |

*D1 protease has been pre-incubated with Z-LDLA-CMK for 1 h at pH 7.0
++ Z-LDLA-CMK is synthesized as described in Example 7.

DETECTING FREE C-TERMINAL D1-TAIL ENZYME PRODUCT

Source of Substrate and D1 Protease

As above, LF-1 thylakoid membranes were isolated and used as enzyme substrate. The source of enzyme was recombinant or native purified Wheat D1-protease.

Molecular Probes

Fluorescamine (Molecular Probe Inc., Eugene, Oreg.) is a molecular probe capable of detecting compounds containing primary amines and were used in this assay method. This probe has the ability to react with N-terinal amines formed on the C-terminal D1-tail portion of the D1 pre-protein, produced as a result of D1 protease action on the substrate.

Assay Method

Assays were run in a 96-well multiscreen plate and prepared as described above.

After incubation with D1 protease the reaction mixture containing the C-terminal D1-tail fragment was transferred to a regular plastic 96-well microtiter plate using a vacuum manifold and pump. The small (approx. size of tail is 1–2 kDa) D1-tail fragment passes through the Durapore® membrane (pore size=0.65 mm) leaving the stacked thyalkoid membranes in the well.

150 mL sodium phosphate buffer (50 mM, pH 8.0) and 50 mL of 1.08 mM fluorescamine in acetone were added to each well and the plate was shaken for 1 min at room temperature. After incubation fluorescence was read on a microtiter plate reader at 400 nm excitation, 460 nm emission.

TABLE 5

| Well with D1 protease | 515 ± 10 relative units |
| --- | --- |
| Well without D1 protease | 470 ± 10 relative units |

Example 10

In vivo high throughput incorporating Scenedesmus mutant and wildtype cells for the detection of a D1 protease inhibitor Example 10 demonstrates an in vivo assay whole cell system to screen for herbicidal agents that target D1 protease. The specific herbicidal agent identified in this example is a known protease inhibitor which comprises a peptide component and will be refered to as IHN-1.

The assay system utilized mutant and wildtype Scenedesmus cells in a reaction mixture that contained a potential D1 protease inhibitor. LF-1 Scenedesmus mutants contain an inactivated D1 protease and are unable to process pre-D1 to the mature protein. Wildtype Scenedesmus contain a functional D1 protease and D1 pre-protein is processed normally. Therefore, in LF-1 cells 100% of D1 protease activity is inhibited. The LF-1 cell shows weaker Fv than that of the wildtype cell [Metz et al., (1980) Biochem. Biophys. Res. Comm. 94, 560 566] upon illumination at high light intensity (10–100 photons per sec per center). Furthermore, it has been shown that the Fi of LF-1 cell is 2–3 fold higher than that of the wildtype cell. When Scenedesmus wildtype cells are illuminated in a suitable growth medium containing a D1 protease inhibitor, Fi-increases and an Fv-decreases.

Assay Method

Wildtype and LF-1 mutant cells were suspended in BG-11 liquid growth medium and placed in 96-well plates, and the cell concentration was adjusted to $OD_{730}=2-3$. D1-protease inhibitor was added to each well and both Fo and Fv fluorescence was measured immediately, using a fluorescence microtiter plate reader.

Plates were then placed under strong illumination ($200\mu$ Einsteins.m$^{-2}$.s$^{-1}$) for 1–3 h, and the fluorescence was measured again. The presence of D1 protease inhibitor is confirmed by an Fi-increase and Fv-decrease in the wildtype cells. No change is observed for LF-1 cells (either with or without inhibitor) after the incubation. The wildtype cells without the addition of inhibitor are used as a 0% inhibition control; and the LF-1 cells are used for 100% inhibition control.

Table 6 shows the relative change in Fo and Fv in incubations of mutant and wildtype cells both with and without a D1 protease inhibitor screened in an in vitro assay.

As can be seen by the data in Table 6 there is no Fo and Fv change for (LF-1+IHN-1), even after a 3 h incubation.

TABLE 6

| Time | Fi-(wt) | Fv-(wt) | Fi-(LF1) | Fv-(LF1) | Fi-(wt + INH-1) | Fv-(wt + INH-1) |
|---|---|---|---|---|---|---|
| 0 h | 20 | 30 | 45 | 24 | 20 | 30 |
| 3 h | 21 | 32 | 45 | 24 | 25 | 29 |

*Fi measurement: excitation, 360 nm/40 nm band width; emission, 665 mm/20 nm band width; Gain, 80; regular fiber optic bundle
*Fv measurement: excitation, 450 nm/50 nm band width; emission, 665 mn/20 nm band width; Gain, 33; visible fiber optic bundle

What is claimed is:

1. A method for identifying a herbicidal agent which inhibits D1 protease comprising:
   a) incubating an effective amount of D1 protease enzyme in a sample suspected of containing a herbicidal agent with an effective amount of unprocessed D1 polypeptide to form a reaction mixture, where, when the D1 protease is not inhibited the unprocessed D1 polypeptide is cleaved into a mature D1 polypeptide and a C-terminal tail;
   b) reacting said reaction mixture with a reporter linked antibody, wherein said antibody complexes with said mature D1 protein and wherein said reporter emits a detectable signal; and
   c) quantitating the amount of D1 protease activity by measuring the detectable signal generated in step (b) wherein the presence or absence of a D1 protease inhibitor is confirmed.

2. The method of claim 1 wherein the effective amount of D1 protease enzyme is at least 10 femtomoles.

3. The method of claim 1 wherein the C-terminal tail of step (a) is reacted with a fluorescent probe whereby an increase in fluorescence indicates D1 protease activity.

4. The method of claim 3 wherein the fluorescent probe is selected from the group consisting of fluorescamine and, 3-(4-carboxybenzoyl)quinoline-2-carboxaldehyde and 3-(2-furoyl)quinoline-2-carboxaldehyde.

5. The method of claim 1 wherein at step (b) said reaction mixture optionally contains a primary antibody having affinity for the mature D1 protein and wherein said reporter linked antibody is a secondary antibody having affinity for said primary antibody.

6. The method of claim 1 wherein at step (b) said reporter linked antibody binds directly to the mature D1 protein.

7. The method of claim 1 wherein the unprocessed D1 polypeptide is contained within a thylakoid membrane and wherein the incubating step a) is performed at about pH 4.0 to about pH 6.0.

8. The method of claim 1 wherein unprocessed D1 polypeptide is contained within a photosystem II core complex and wherein said incubating step a) is performed at about pH 6.0 to about pH 8.0.

9. The method of claim 1 wherein the suitable D1 enzyme substrate is immobilized on a suitable support.

10. The method of claim 1 wherein the suitable D1 enzyme substrate is in solution or homogeneously suspended.

11. The method of claim 9 wherein said suitable support is selected from group consisting of polystyrene, substituted polystyrene, polypropylene, polyglycidylmethacrylate, agarose, nitrocellulose, nylon, magnetic and non-magnetic particles.

12. The method of claim 1 wherein the D1 protease enzyme is isolated from an organism selected from the group consisting of higher plants, algae, cyanobacteria, and recombinant organisms expressing at least one gene encoding a D1 protease enzyme.

13. The method of claim 12 wherein the D1 protease enzyme is isolated from a higher plant selected from the group consisting of soybean, rapeseed, sunflower, cotton, corn, tobacco, alfalfa, wheat, barley, oats, sorghum, rice, cruciferous vegetables, broccoli, cauliflower, cabbage, parsnips, tomato, potato, spinach, alfalfa, sorghum, hardwood and softwood trees, and forage grasses.

14. The method of claim 12 wherein the D1 protease enzyme is isolated from an organism selected from the group consisting of wheat, Scenedesmus, Synechocystis, tobacco, and spinach.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: PRIMER A ( x i ) SEQUENCE DESCRIPTION: SEQ ID NO:1:

GAAGGCTGGC AGGCGTGA                                                                18

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: PRIMER B ( x i ) SEQUENCE DESCRIPTION: SEQ ID NO:2:

CCAGTCGCGC ATAGTAAGTA TACTC                                                        25

( 2 ) INFORMATION FOR SEQ ID NO:3:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: SCENEDESMUS GENE ( x i ) SEQUENCE DESCRIPTION: SEQ ID NO:3:

```
GGGGTACTCC  CGGACAAACT  GCTTGCAAAC  CAGCGTCCGA  GCACCGCAAC  CACACTTCAG    60
GCCATTTACT  GCAGTCAAAA  CATGTAGACA  GCGGTGCAGC  ACAACTGCAG  CAGCAGCCAA   120
GCGTGATCAG  GCGCAAGAAC  AGCAGCCATG  GATTCAGGTT  GGGCTGGGCC  TGGCAGCTGC   180
TGCCACTGCA  GTGGCAGTGG  GCCTGGGGGC  AGCTGCGCTG  CCGGCGCAAG  CAGTGACAAG   240
CGAGCAGCTG  CTGTTCCTGG  AAGCATGGCG  AGCAGTGGAC  AGGGCTTATG  TGGACAAATC   300
GTTCAACGGG  CAGAGCTGGT  TCAAGCTACG  GGAGACGTAC  CTTAAGAAGG  AGCCCATGGA   360
CAGGCGGGCG  CAGACATATG  ATGCCATCCG  CAAGCTGCTG  GCGGTGCTGG  ACGACCCCTT   420
CACGCGCTTC  TTGGAGCCCT  CACGCCTGGC  TGCGCTGCGG  CGAGGCACAG  CAGGCTCTGT   480
TACAGGTGTA  GGCTTGGAGA  TAACGTATGA  CGGCGGCAGC  GGCAAAGACG  TTGTAGTGCT   540
GACGCCTGCG  CCTGGCGGGC  CGGCAGAGAA  GGCTGGTGCA  CGGGCTGGTG  ATGTCATTGT   600
GACAGTGGAT  GGCACGGCTG  TGAAGGGGCT  GTCGCTGTAT  GACGTGTCTG  ATTTGCTGCA   660
AGGAGAGGCT  GACTCACAGG  TGGAGGTGGT  GCTGCATGCG  CCTGGAGCAC  CCAGCAACAC   720
GCGCACGCTG  CAGCTGACGC  GCCAGAAAGT  GACCATCAAC  CCAGTCACGT  TCACCACCTG   780
CAGCAACGTG  GCAGCAGCAG  CACTGCCTCC  AGGTGCCGCG  AAGCAGCAGC  TGGGCTATGT   840
GCGGCTGGCC  ACCTTCAACA  GCAACACCAC  AGCAGCAGCA  CAGCAGGCGT  TCACAGAGCT   900
GAGCAAGCAG  GGCGTGGCTG  GCTTGGTGCT  GGACATACGC  AACAACGGCG  GCGGCCTGTT   960
CCCAGCAGGT  GTGAACGTGG  CGCGCATGCT  GGTGGACCGG  GGTGATTTGG  TGCTCATCGC  1020
GGACAGCCAG  GGCATCCGTG  ACATCTACTC  GGCTGACGGC  AACAGCATCG  ACAGTGCCAC  1080
GCCGCTGGTG  GTGCTGGTCA  ACAGGGGCAC  AGCCTCCGCC  TCAGAGGTGC  TTGCTGGCGC  1140
GCTGAAGGAC  AGCAAGCGGG  GCCTCATAGC  TGGCGAGCGC  ACCTTTGGCA  AGGGCCTCAT  1200
TCAGACTGTG  GTGGACTTGT  CGGATGGCTC  TGGCGTGGCT  GTGACGGTTG  CGCGGTACCA  1260
GACGCCAGCT  GGCGTTGACA  TCAACAAGAT  AGGTGTCAGT  CCAGATGTGC  AGCTTGACCC  1320
AGAGGTGCTG  CCGACAGATC  TGGAGGGGGT  GTGCCGCGTG  CTGGGGTCTG  ATGCTGCGCC  1380
GCGGCTGTTT  GGGTGAGCTG  TCACAGCAGT  GTGTGGCTGC  AGGGTGTGTT  CGTGCGCGGG  1440
GGCGCACACG  GCACTGCAAG  CGTTTGTAGG  GCAACCGGCA  CTCGAGCAGC  GTTGTGACAG  1500
CACGCGTCGT  TGTCAGCTCG  TGTGAGCATC  AGCAACCCCG  GACAACAAGC  AGCAGCAGCA  1560
CTCGGGCGTG  CGTGTCCCTG  CACGGTCAGC  TGCACACAGT  TGGCGCGATG  GATTTGCTTG  1620
TCATTGCTTG  CTGGCTGTCG  TGGAACGTGG  ACCTGCATAC  ATATCACCTT  GAAATGATCA  1680
```

( 2 ) INFORMATION FOR SEQ ID NO:4:

( i ) SEQUENCE CHARACTERISTICS:
        ( A ) LENGTH: 387 amino acids
        ( B ) TYPE: amino acid
        ( C ) STRANDEDNESS: unknown
        ( D ) TOPOLOGY: unknown ( i i ) MOLECULE TYPE: protein ( v i ) ORIGINAL SOURCE:
        ( B ) STRAIN: SCENEDESMUS D1 PROTEASE PROTEIN ( x i ) SEQUENCE DESCRIPTION: SEQ ID NO:4:

```
Val  Thr  Ser  Glu  Gln  Leu  Leu  Phe  Leu  Glu  Ala  Trp  Arg  Ala  Val  Asp
 1             5                        10                       15

Arg  Ala  Tyr  Val  Asp  Lys  Ser  Phe  Asn  Gly  Gln  Ser  Trp  Phe  Lys  Leu
                20                       25                       30
```

```
Arg Glu Thr Tyr Leu Lys Lys Glu Pro Met Asp Arg Arg Ala Gln Thr
         35                  40                    45
Tyr Asp Ala Ile Arg Lys Leu Leu Ala Val Leu Asp Asp Pro Phe Thr
     50              55                  60
Arg Phe Leu Glu Pro Ser Arg Leu Ala Ala Leu Arg Arg Gly Thr Ala
 65              70                  75                      80
Gly Ser Val Thr Gly Val Gly Leu Glu Ile Thr Tyr Asp Gly Gly Ser
                 85                  90                  95
Gly Lys Asp Val Val Val Leu Thr Pro Ala Pro Gly Gly Pro Ala Glu
             100             105             110
Lys Ala Gly Ala Arg Ala Gly Asp Val Ile Val Thr Val Asp Gly Thr
         115             120             125
Ala Val Lys Gly Leu Ser Leu Tyr Asp Val Ser Asp Leu Leu Gln Gly
     130             135             140
Glu Ala Asp Ser Gln Val Glu Val Val Leu His Ala Pro Gly Ala Pro
145             150             155                 160
Ser Asn Thr Arg Thr Leu Gln Leu Thr Arg Gln Lys Val Thr Ile Asn
             165             170             175
Pro Val Thr Phe Thr Thr Cys Ser Asn Val Ala Ala Ala Leu Pro
             180             185             190
Pro Gly Ala Ala Lys Gln Gln Leu Gly Tyr Val Arg Leu Ala Thr Phe
         195             200             205
Asn Ser Asn Thr Thr Ala Ala Ala Gln Gln Ala Phe Thr Glu Leu Ser
210             215             220
Lys Gln Gly Val Ala Gly Leu Val Leu Asp Ile Arg Asn Asn Gly Gly
225             230             235                 240
Gly Leu Phe Pro Ala Gly Val Asn Val Ala Arg Met Leu Val Asp Arg
             245             250             255
Gly Asp Leu Val Leu Ile Ala Asp Ser Gln Gly Ile Arg Asp Ile Tyr
             260             265             270
Ser Ala Asp Gly Asn Ser Ile Asp Ser Ala Thr Pro Leu Val Val Leu
             275             280             285
Val Asn Arg Gly Thr Ala Ser Ala Ser Glu Val Leu Ala Gly Ala Leu
     290             295             300
Lys Asp Ser Lys Arg Gly Leu Ile Ala Gly Glu Arg Thr Phe Gly Lys
305                 310             315                     320
Gly Leu Ile Gln Thr Val Val Asp Leu Ser Asp Gly Ser Gly Val Ala
             325             330             335
Val Thr Val Ala Arg Tyr Gln Thr Pro Ala Gly Val Asp Ile Asn Lys
             340             345             350
Ile Gly Val Ser Pro Asp Val Gln Leu Asp Pro Glu Val Leu Pro Thr
         355             360             365
Asp Leu Glu Gly Val Cys Arg Val Leu Gly Ser Asp Ala Ala Pro Arg
     370             375             380
Leu Phe Gly
385
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ATGGACTATC TTACTGACTG C                                                                 2 1

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCTGAATCTT CGAATTGCCC CTTC                                                              2 4

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TCTGAACCTG GAATCTCACA CATCCTTGA                                                         2 9

( 2 ) INFORMATION FOR SEQ ID NO:8:

( i ) SEQUENCE CHARACTERISTICS:
        ( A ) LENGTH: 1164 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: WHEAT D1 PROTEASE GENE ( x i ) SEQUENCE DESCRIPTION: SEQ ID NO:8:

CTCACGGAGG AGAACCTGCT GTTCCTGGAG GCGTGGCGCG CGGTGGACCG CGCCTACTAC        6 0

GACAAGTCCT TCAACGGGCA GAGCTGGTTC AGGTACCGCG AGCGCGCCCT CCGCGACGAC        1 2 0

CCCATGAACA CGCGGCAGGA GACATATGCG GCGATTAAGA AAATGCTTGC AACCTTGGAT        1 8 0

GATCCGTTCA CTCGGTTATT GGAACCCGAG AAATTCAAGA GTTTGCGGTC TGGCACGCAA        2 4 0

GGTGCCCTCA CGGGTGTAGG TTTATCCATC GGCTACCCGT TGGCCCTTAA AGGATCACCT        3 0 0

GCAGGGCTCT CCGTAATGTC AGCAGCCCCA GGGGGTCCTG CAGAAAAGGC GGGCATTGTG        3 6 0

TCTGGAGACG TTATTTTGGC AATTGACGAC ACAAGCGCAC AAGACATGGA CATATATGAC        4 2 0

GCAGCAGATC GCTTACAGGG TCCTGAAGGA AGCTCAATAG ATTTGACTAT TCTCAGTGGA        4 8 0

GCTGATACCA GACATGTTGT TTTGAAGCGA GAAAGATATA CTTTAAACCC GGTGAGGTCA        5 4 0

AGGATGTGTG AGATTCCAGG TTCAGAGGAT AGCTCAAAGA TTGGTTACAT CAAACTAACA        6 0 0

ACATTTAACC AAAATGCTGC AGGGTCTGTT AAGGAAGCCA TTAAGAAATT AAGGGAGAAA        6 6 0

AACGTAAAGG CCTTTGTGTT GGATCTGCGG AATAACAGCG GTGGTCTTTT TCCCGAAGGG        7 2 0

ATTGAGATTG CGAAGATTTG GATGGACAAG GGTGTCATTG TGTATATATG TGATAGCCGT        7 8 0

GGTGTCCGTG ACATTTATGA GGCAGATGGA GCTAGCACGA TTGCTGCATC AGAACCTTTA        8 4 0

GTTGTCCTGG TAAACAAAGG AACCGCAAGT GCAAGTGAGA TCCTTGCAGG AGCACTGAAA        9 0 0

```
GACAACAAGA  GGGCAGTGGT  GTATGGGGAA  CCAACATATG  GAAAAGGCAA  GATCCAGTCG    960

GTGTTTGCAC  TGTCCGATGG  CTCAGGGTTG  GCCGTGACGG  TGGCGCGCTA  CGAAACCCCT   1020

GCGCATACTG  ACATAGATAA  GGTCGGTGTG  ACTCCGGACC  GTCCATTGCC  GGCATCATTC   1080

CCGACCGACG  AGGATGGCTT  CTGCAGCTGC  CTCAGGGACC  CAGCTTCTTG  CAACCTTAAT   1140

GCTGCCCGGC  TGTTTGTGAG  ATCG                                             1164
```

( 2 ) INFORMATION FOR SEQ ID NO:9:

( i ) SEQUENCE CHARACTERISTICS:
        ( A ) LENGTH: 388 amino acids
        ( B ) TYPE: amino acid
        ( C ) STRANDEDNESS: unknown
        ( D ) TOPOLOGY: unknown ( i i ) MOLECULE TYPE: protein ( v i ) ORIGINAL SOURCE:
        ( B ) STRAIN: WHEAT D1 PROTEASE PROTEIN ( x i ) SEQUENCE DESCRIPTION: SEQ ID NO:9:

```
Leu  Thr  Glu  Glu  Asn  Leu  Leu  Phe  Leu  Glu  Ala  Trp  Arg  Ala  Val  Asp
 1              5                        10                       15

Arg  Ala  Tyr  Tyr  Asp  Lys  Ser  Phe  Asn  Gly  Gln  Ser  Trp  Phe  Arg  Tyr
                20                       25                       30

Arg  Glu  Arg  Ala  Leu  Arg  Asp  Asp  Pro  Met  Asn  Thr  Arg  Gln  Glu  Thr
           35                       40                       45

Tyr  Ala  Ala  Ile  Lys  Lys  Met  Leu  Ala  Thr  Leu  Asp  Asp  Pro  Phe  Thr
      50                       55                       60

Arg  Leu  Leu  Glu  Pro  Glu  Lys  Phe  Lys  Ser  Leu  Arg  Ser  Gly  Thr  Gln
65                       70                       75                       80

Gly  Ala  Leu  Thr  Gly  Val  Gly  Leu  Ser  Ile  Gly  Tyr  Pro  Leu  Ala  Leu
                85                       90                       95

Lys  Gly  Ser  Pro  Ala  Gly  Leu  Ser  Val  Met  Ser  Ala  Ala  Pro  Gly  Gly
               100                      105                      110

Pro  Ala  Glu  Lys  Ala  Gly  Ile  Val  Ser  Gly  Asp  Val  Ile  Leu  Ala  Ile
          115                      120                      125

Asp  Asp  Thr  Ser  Ala  Gln  Asp  Met  Asp  Ile  Tyr  Asp  Ala  Ala  Asp  Arg
     130                      135                      140

Leu  Gln  Gly  Pro  Glu  Gly  Ser  Ser  Ile  Asp  Leu  Thr  Ile  Leu  Ser  Gly
145                      150                      155                      160

Ala  Asp  Thr  Arg  His  Val  Val  Leu  Lys  Arg  Glu  Arg  Tyr  Thr  Leu  Asn
                165                      170                      175

Pro  Val  Arg  Ser  Arg  Met  Cys  Glu  Ile  Pro  Gly  Ser  Glu  Asp  Ser  Ser
               180                      185                      190

Lys  Ile  Gly  Tyr  Ile  Lys  Leu  Thr  Thr  Phe  Asn  Gln  Asn  Ala  Ala  Gly
          195                      200                      205

Ser  Val  Lys  Glu  Ala  Ile  Lys  Lys  Leu  Arg  Glu  Lys  Asn  Val  Lys  Ala
     210                      215                      220

Phe  Val  Leu  Asp  Leu  Arg  Asn  Asn  Ser  Gly  Gly  Leu  Phe  Pro  Glu  Gly
225                      230                      235                      240

Ile  Glu  Ile  Ala  Lys  Ile  Trp  Met  Asp  Lys  Gly  Val  Ile  Val  Tyr  Ile
                245                      250                      255

Cys  Asp  Ser  Arg  Gly  Val  Arg  Asp  Ile  Tyr  Glu  Ala  Asp  Gly  Ala  Ser
               260                      265                      270

Thr  Ile  Ala  Ala  Ser  Glu  Pro  Leu  Val  Val  Leu  Val  Asn  Lys  Gly  Thr
          275                      280                      285
```

| Ala | Ser | Ala | Ser | Glu | Ile | Leu | Ala | Gly | Ala | Leu | Lys | Asp | Asn | Lys | Arg |
|---|---|---|---|---|---|---|---|---|---|---|---|---|---|---|---|
| | 290 | | | | 295 | | | | | 300 | | | | | |

| Ala | Val | Val | Tyr | Gly | Glu | Pro | Thr | Tyr | Gly | Lys | Gly | Lys | Ile | Gln | Ser |
|---|---|---|---|---|---|---|---|---|---|---|---|---|---|---|---|
| 305 | | | | | 310 | | | | 315 | | | | | 320 | |

| Val | Phe | Ala | Leu | Ser | Asp | Gly | Ser | Gly | Leu | Ala | Val | Thr | Val | Ala | Arg |
|---|---|---|---|---|---|---|---|---|---|---|---|---|---|---|---|
| | | | | 325 | | | | 330 | | | | | 335 | | |

| Tyr | Glu | Thr | Pro | Ala | His | Thr | Asp | Ile | Asp | Lys | Val | Gly | Val | Thr | Pro |
|---|---|---|---|---|---|---|---|---|---|---|---|---|---|---|---|
| | | | 340 | | | | 345 | | | | | 350 | | | |

| Asp | Arg | Pro | Leu | Pro | Ala | Ser | Phe | Pro | Thr | Asp | Glu | Asp | Gly | Phe | Cys |
|---|---|---|---|---|---|---|---|---|---|---|---|---|---|---|---|
| | | 355 | | | | | 360 | | | | | 365 | | | |

| Ser | Cys | Leu | Arg | Asp | Pro | Ala | Ser | Cys | Asn | Leu | Asn | Ala | Ala | Arg | Leu |
|---|---|---|---|---|---|---|---|---|---|---|---|---|---|---|---|
| | 370 | | | | | 375 | | | | 380 | | | | | |

| Phe | Val | Arg | Ser |
|---|---|---|---|
| 385 | | | |

(2) INFORMATION FOR SEQ ID NO:10:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

GGTCGGAAGG ATCTGGGTGT C                                                        21

(2) INFORMATION FOR SEQ ID NO:11:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

ATAGTAAGCC CACACAGTTT CTC                                                      23

(2) INFORMATION FOR SEQ ID NO:12:

(i) SEQUENCE CHARACTERISTICS:
    (A) LENGTH: 1485 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (B) STRAIN: SYNECHOCYSTIS D1 PROTEASE GENE (xi) SEQUENCE DESCRIPTION: SEQ ID NO:12:

ACCTAGTAGT CAAGGACTCT AAGCACCGCC CCGGGGTTTA TTTTCTTAAC TAATCTTCTT              60

CAACGGTCCG GTAAATCTCA TGTTGAAGCA AAAGCGCAGT CTAATTTTGG GAACTACAGC             120

TCTGTTATTG ACAACAGTGG CGGTGACGGG GGTTGGGTTG CGATTGGCCC GCTCCCAGGG             180

CTACCTACAG GATAATCTCA AGGAGCTGGT TGACGAAGTT TGGCAAATTG TCGACCACAC             240

CTATGTAGAT GGTACTTTCA ACGGTGAGGA TTGGGTAGCG GTTCGCCAGG ATTATCTAAC             300

ACGGGACTAC AAAAACCAGG AAGAAGCCTA CACCGCCATT CGGGAAATGC TGGAGAAGCT             360

```
AAATGACCCC  TACACTCGCT  TCATGTCCCC  CGATGAGTTT  CAATCAATGC  GTATCGACAC    420
TTCCGGTGAA  TTGACCGGGG  TGGGTATTCA  AATCACCCAG  GACCAGGATA  CGAAGAAAAT    480
TGTGGTGGTG  GCTCCCATCG  AAGATACCCC  CGCCTACAAC  GCTGGCATTC  TTTCTAAGGA    540
CATAATTACC  AAGATTGACG  GTAAGTCCAC  CGATGGCATG  GAAGTAGATG  ACGCAGTGAA    600
GTTAATTCGG  GGTAAGCCCG  GCACCAGTGT  GGCGCTCACT  ATTGAGCGGG  AAGGGCAGGC    660
GATCGAATAT  CCTTTGACCC  GGACTTTAAT  TAAAATTCAT  CCAGTGCGGG  CCCAAGTGGA    720
AGATATTAAT  GGTGCCAGGG  TTGGTTATAT  CCGTTTAAAT  CAATCCAGTG  CCCAGGCTTC    780
GGAGGAAATG  CGCCAAGCAG  TGCAGAAATT  GAAAAAGAG  AATGTGGTCG  GCTACATTTT    840
TGACCTGCGT  TCCAATCCCG  GTGGTTTGAT  CTATCCCAGT  GCGAATATCG  CTCGCATTTG    900
GTTGGATGAA  GGGGGCATTG  TGTCCACCGT  CGATCGCCGA  GGGGAAGTGG  AACAACAAAG    960
TGCTAACAAG  CGACAGTCGA  GTAACCGTCC  CCTAGTGGCG  TCGACGAATG  GCGGTTCCGC   1020
CAGCGCCAAT  AAAATCATCT  CCGGGGCCTT  ACAGAATAAT  CAACGGGCCG  TCATCGTGGG   1080
CACCAAAACC  TTTGATAAGG  AATTAGTACA  ATCGGTGCGG  GAGTTGGGGG  ATGGTTCCGG   1140
TATGGCAGTG  ACGATCGCCA  AATATTTAAT  CCCCAACGGT  CGGGACATCA  ATAAACATGG   1200
CATCGACCCC  TATGTGGAAG  TAGAACTCAC  CGACGCCCAG  CGGAAGGAAT  TGCAACAAAA   1260
TCGGGAAAAA  GTAGGCACCC  TGGAAGACCC  CCAATTTGCC  AGGGCCTATG  AAGTGCTAAT   1320
GCAACAGGTG  AACAAAACCG  CTTCTAAGTA  GCTTAAGTAG  GTTGAACGAG  CTTGTACAAT   1380
TTCATTCGGT  AAAAGTCTAT  GGTTCAAACT  GCCCTACTTC  CCCTCGACTT  TCCCGATCTA   1440
TATCCGGAAT  CCGACGGTAA  ACCCATGGCT  GACAATACCC  TGCAG                    1485
```

(2) INFORMATION FOR SEQ ID NO:13:
    (i) SEQUENCE CHARACTERISTICS:
        (A) LENGTH: 391 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (B) STRAIN: SYNECHOCYSTIS D1 PROTEASE PROTEIN (xi) SEQUENCE DESCRIPTION: SEQ ID NO:13:

```
Gln Gly Tyr Leu Gln Asp Asn Pro Lys Glu Leu Val Asp Glu Val Trp
 1               5                  10                  15

Gln Ile Val Asn Arg Thr Tyr Val Asp Gly Thr Phe Asn Gly Glu Asp
            20                  25                  30

Trp Val Ala Val Arg Gln Asp Tyr Leu Thr Arg Asp Tyr Lys Asn Gln
        35                  40                  45

Glu Glu Ala Tyr Thr Ala Ile Arg Glu Met Leu Glu Lys Leu Asn Asp
    50                  55                  60

Pro Tyr Thr Arg Phe Met Ser Pro Asp Glu Phe Gln Ser Met Arg Ile
65                  70                  75                  80

Asp Thr Ser Gly Glu Leu Thr Gly Val Gly Ile Gln Ile Thr Gln Asp
                85                  90                  95

Gln Asp Thr Lys Lys Ile Val Val Val Ala Pro Ile Glu Asp Thr Pro
            100                 105                 110

Ala Tyr Asn Ala Gly Ile Leu Ser Lys Asp Ile Ile Thr Lys Ile Asp
        115                 120                 125

Gly Lys Ser Thr Asp Gly Met Glu Val Asp Asp Ala Val Lys Leu Ile
    130                 135                 140
```

```
Arg  Gly  Lys  Pro  Gly  Thr  Ser  Val  Ala  Leu  Thr  Ile  Glu  Arg  Glu  Gly
145                 150                      155                          160

Gln  Ala  Ile  Glu  Tyr  Pro  Leu  Thr  Arg  Thr  Leu  Ile  Glu  Ile  His  Pro
                    165                 170                          175

Val  Arg  Ala  Gln  Val  Glu  Asp  Ile  Asn  Gly  Ala  Arg  Val  Gly  Tyr  Ile
               180                      185                     190

Arg  Leu  Asn  Gln  Phe  Ser  Ala  Gln  Ala  Ser  Glu  Glu  Met  Arg  Gln  Ala
          195                      200                     205

Val  Gln  Lys  Leu  Glu  Lys  Glu  Asn  Val  Val  Gly  Tyr  Ile  Phe  Asp  Leu
     210                 215                     220

Arg  Ser  Asn  Pro  Gly  Gly  Leu  Leu  Tyr  Ser  Ser  Val  Asp  Ile  Ala  Arg
225                 230                      235                         240

Ile  Trp  Leu  Asp  Glu  Gly  Gly  Ile  Val  Ser  Thr  Val  Asp  Arg  Arg  Gly
               245                      250                         255

Glu  Val  Glu  Gln  Gln  Ser  Ala  Asn  Lys  Arg  Gln  Leu  Ser  Asn  Arg  Pro
               260                      265                     270

Leu  Val  Val  Leu  Val  Asp  Gly  Gly  Ser  Pro  Ser  Ala  Ser  Glu  Ile  Val
          275                      280                     285

Ser  Gly  Ala  Leu  Gln  Asp  Asn  Gln  Arg  Ala  Val  Ile  Val  Gly  Thr  Lys
     290                      295                     300

Thr  Phe  Gly  Lys  Gly  Leu  Val  Gln  Ser  Val  Arg  Glu  Leu  Gly  Asp  Gly
305                      310                     315                         320

Ser  Gly  Met  Ala  Val  Thr  Ile  Ala  Lys  Tyr  Leu  Thr  Pro  Asn  Gly  Arg
               325                      330                          335

Asp  Ile  Asn  Lys  His  Gly  Ile  Asp  Pro  Asp  Val  Glu  Val  Glu  Leu  Thr
               340                      345                     350

Asp  Ala  Gln  Arg  Lys  Glu  Leu  Gln  Gln  Asn  Arg  Glu  Lys  Val  Gly  Thr
               355                      360                     365

Leu  Glu  Asp  Pro  Gln  Phe  Ala  Arg  Ala  Tyr  Glu  Val  Leu  Met  Gln  Gln
370                      375                     380

Val  Asn  Lys  Thr  Ala  Ser  Lys
385                      390
```

(2) INFORMATION FOR SEQ ID NO:14:

(i) SEQUENCE CHARACTERISTICS:
        (A) LENGTH: 1994 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: TOBACCO D1 PROTEASE GENE (xi) SEQUENCE DESCRIPTION: SEQ ID NO:14:

```
AGGAATTCGG  CACGAGACTA  GAAAAAGGGG  ATAAGAGAAG  GAAAAAAAAG  AAAGAAGCAA    60
AACGATAACA  AACAGAATTG  AAAACGAAAT  TGAGCAATGG  AAGCTCTTCT  GGAAGCTCT   120
CATTCTCCTT  CAGCCTCTGT  ATCTCCTTCA  TTCATCATCA  CCAGTAGCTA  TAGAAAAAAC  180
CCCACCATTG  CGTTTAAGGT  GCTTTCGTGG  ATTCTTTGTA  CAGTGGAAGT  AATAACTCTC  240
GACTATATCC  TCCTATATTG  TGTCTTAAAA  AGAGTGGCAA  TGACAACTCT  GGAAGTTGCT  300
CTCCTTCATA  CTGCATTGAG  CAAATGTGCA  GAAACAAAAT  GTTTTCTCAG  CCAAACTGGA  360
GGCATAGCAA  ACTATTCATT  GATAAGCAAA  GTTTTCTGGT  TACACAAAAT  GGCTTAGCTT  420
TTCTACCAAG  AAAATTCAGA  ACCATTCTCC  GCAAAACAGT  AAAACATTCA  GAAATATTTA  480
```

|  |  |  |  |  |  |
|---|---|---|---|---|---|
| GGAATATAGT | ACCTGATATA | TTTGTTCGGT | CCTGCATTGG | ACTAATGCTG | GTTATGGCAC | 540 |
| TTAATGCTGC | TGTTGCAAAA | GCTCCTTCTT | TTGCTCTCAC | TGAACAAAAT | CTGCTTTTCT | 600 |
| TGGAGGCATG | GAGAACAATT | GACCGTGCAT | ATATTGACAA | GACCTTCAAT | GGTCAAAGTT | 660 |
| GGTTTAGGTA | CAGAGAAGAT | GCACTACGGA | AAGAACCAAT | GAACACTAGA | CAGGAAACGT | 720 |
| ATGCAGCAAT | AAAAAGATG | ATTGCCACTC | TGGATGACCC | TTTTACCCGT | TTTCTGGAGC | 780 |
| CTGAAAAGTT | TAAAAGTTTG | CGGTCCGGAA | CTCAAAATGC | ACTTACTGGA | GTAGGGTTGT | 840 |
| CAATTGGCTA | TCCAACAGGA | AAAACTGAAT | CAGCTCCTGG | ACTGGTCGTC | GTCTCAGCTT | 900 |
| CTCCAGGAGG | TTCTGCAGAT | AGGGTCTGGC | ATCTCATCGG | TGATATTATC | CTAGAAATTG | 960 |
| ACAATTCCAG | CACAGATAAC | ATGGGTATAT | ATGATGCAGC | AGAACGGTTA | CAAGGACCTG | 1020 |
| AAGGAAGTGG | TGTGGAACTA | ACTGTACGTC | GTGGATCCGA | GACAAGGAAC | CTACCATTGA | 1080 |
| TACGGGAGAA | AGTTTTGCTT | AATCCTGTAA | AATCAAGAAT | CTGCAAGCTG | CCCACGGGAG | 1140 |
| GAGATGATGC | TCCACAGATT | GGATACATCA | AACTATCAAC | ATTCAACCAA | AATGCTTCTG | 1200 |
| GTGCTGTAAG | AGAAGCGATC | GAAGCCTTAA | GGAAAAACAA | TGTTAATGCC | TTTGTGTTGG | 1260 |
| ACCTTCGGGA | TAATAGTGGT | GGTCTCTTCC | CAGAAGGAGT | TGAGATACGA | AAAATTTGGT | 1320 |
| TAAACAAGGG | TGTGATTGTA | TACATTTGTG | ATAGCCGTGG | TGTTCGAGAT | ATTTATGACA | 1380 |
| CGGATGGGAG | CAATGTGGTA | GCTGCTTCAG | AACCCCTAGC | AGTGCTGGTA | AACAAAGGA | 1440 |
| CTGCAAGCGC | AAGTGAGATT | TTAGCAGGTG | CTTTGAAAGA | TAATAAGCGA | GCCCAGCTTT | 1500 |
| TTGGTGAACC | AACATATGGC | AAGGGTAAAA | TCCAGTCAGT | ATTCCAGCTA | TCAGATGGCT | 1560 |
| CTGGCTTGGC | TGTTACAGTT | GCTCGGTATG | AAACTCCTGC | TCACAACGAT | ATAGACAAGG | 1620 |
| TTGGTGTAAT | TCCGGACCAT | CCTTTGCCAG | CTTCATTCCC | AAAAGACGAC | GAGAGCTTCT | 1680 |
| GTAACTGCCT | TCTAAATCCT | GCCTCTGCTT | GCCACCTAAA | CAGAGTCGAG | CTATTCTCGA | 1740 |
| AATAACTACA | TCCCTACAGT | CTGAAGAAAA | GATCTTGTTT | TTCAACTTGT | GTTTGTAGAT | 1800 |
| TCCATAGTTT | CCATTTGATT | CTTTTGGCAG | ATGCAAGTTG | GTGATTTTGC | TTGCATGCAT | 1860 |
| CTGATGTCTG | TACATACCAT | GAACAAAGGA | CAACTTCAAT | TTCTATTGTT | GAACTCTTGC | 1920 |
| TGTAATAGAA | TCAAATTCAA | TAGTTTATCA | ATCATCTTTT | GAACTCTAAA | GCAAAAAAAA | 1980 |
| AAAAAAAAAC | TCGA |  |  |  |  | 1994 |

( 2 ) INFORMATION FOR SEQ ID NO:15:

( i ) SEQUENCE CHARACTERISTICS:
    ( A ) LENGTH: 473 amino acids
    ( B ) TYPE: amino acid
    ( C ) STRANDEDNESS: unknown
    ( D ) TOPOLOGY: unknown ( i i ) MOLECULE TYPE: protein ( v i ) ORIGINAL SOURCE:
    ( B ) STRAIN: TOBACCO D1 PROTEASE PROTEIN ( x i ) SEQUENCE DESCRIPTION: SEQ ID NO:15:

```
Met Cys Arg Asn Lys Met Phe Ser Gln Pro Asn Trp Arg His Ser Lys
 1               5                  10                  15

Leu Phe Ile Asp Lys Gln Ser Phe Leu Val Thr Gln Asn Gly Leu Ala
            20                  25                  30

Phe Leu Pro Arg Lys Phe Arg Thr Ile Leu Arg Lys Thr Val Lys His
        35                  40                  45

Ser Glu Ile Phe Arg Asn Ile Val Pro Asp Ile Phe Val Arg Ser Cys
    50                  55                  60
```

| | | | | | | | | | | | | | | |
|---|---|---|---|---|---|---|---|---|---|---|---|---|---|---|
| Ile | Gly | Leu | Met | Leu | Val | Met | Ala | Leu | Asn | Ala | Ala | Val | Ala | Lys | Ala |
| 65 | | | | 70 | | | | | 75 | | | | | 80 | |
| Pro | Ser | Phe | Ala | Leu | Thr | Glu | Gln | Asn | Leu | Leu | Phe | Leu | Glu | Ala | Trp |
| | | | | 85 | | | | | 90 | | | | | 95 | |
| Arg | Thr | Ile | Asp | Arg | Ala | Tyr | Ile | Asp | Lys | Thr | Phe | Asn | Gly | Gln | Ser |
| | | | 100 | | | | | 105 | | | | | 110 | | |
| Trp | Phe | Arg | Tyr | Arg | Glu | Asp | Ala | Leu | Arg | Lys | Glu | Pro | Met | Asn | Thr |
| | | 115 | | | | | 120 | | | | | 125 | | | |
| Arg | Gln | Glu | Thr | Tyr | Ala | Ala | Ile | Lys | Lys | Met | Ile | Ala | Thr | Leu | Asp |
| | 130 | | | | | 135 | | | | | 140 | | | | |
| Asp | Pro | Phe | Thr | Arg | Phe | Leu | Glu | Pro | Glu | Lys | Phe | Lys | Ser | Leu | Arg |
| 145 | | | | | 150 | | | | | 155 | | | | | 160 |
| Ser | Gly | Thr | Gln | Asn | Ala | Leu | Thr | Gly | Val | Gly | Leu | Ser | Ile | Gly | Tyr |
| | | | | 165 | | | | | 170 | | | | | 175 | |
| Pro | Thr | Gly | Lys | Thr | Glu | Ser | Ala | Pro | Gly | Leu | Val | Val | Val | Ser | Ala |
| | | | 180 | | | | | 185 | | | | | 190 | | |
| Ser | Pro | Gly | Gly | Ser | Ala | Asp | Arg | Val | Trp | His | Leu | Ile | Gly | Asp | Ile |
| | | 195 | | | | | 200 | | | | | 20 | | | |
| Ile | Leu | Glu | Ile | Asp | Asn | Ser | Ser | Thr | Asp | Asn | Met | Gly | Ile | Tyr | Asp |
| | 210 | | | | | 215 | | | | | 220 | | | | |
| Ala | Ala | Glu | Arg | Leu | Gln | Gly | Pro | Glu | Gly | Ser | Gly | Val | Glu | Leu | Thr |
| 225 | | | | | 230 | | | | | 235 | | | | | 240 |
| Val | Arg | Arg | Gly | Ser | Glu | Thr | Arg | Asn | Leu | Pro | Leu | Ile | Arg | Glu | Lys |
| | | | | 245 | | | | | 250 | | | | | 255 | |
| Val | Leu | Leu | Asn | Pro | Val | Lys | Ser | Arg | Ile | Cys | Lys | Leu | Pro | Thr | Gly |
| | | | 260 | | | | | 265 | | | | | 270 | | |
| Gly | Asp | Asp | Ala | Pro | Gln | Ile | Gly | Tyr | Ile | Lys | Leu | Ser | Thr | Phe | Asn |
| | | 275 | | | | | 280 | | | | | 285 | | | |
| Gln | Asn | Ala | Ser | Gly | Ala | Val | Arg | Glu | Ala | Ile | Glu | Ala | Leu | Arg | Lys |
| | 290 | | | | | 295 | | | | | 300 | | | | |
| Asn | Asn | Val | Asn | Ala | Phe | Val | Leu | Asp | Leu | Arg | Asp | Asn | Ser | Gly | Gly |
| 305 | | | | | 310 | | | | | 315 | | | | | 320 |
| Leu | Phe | Pro | Glu | Gly | Val | Glu | Ile | Arg | Lys | Ile | Trp | Leu | Asn | Lys | Gly |
| | | | | 325 | | | | | 330 | | | | | 335 | |
| Val | Ile | Val | Tyr | Ile | Cys | Asp | Ser | Arg | Gly | Val | Arg | Asp | Ile | Tyr | Asp |
| | | | 340 | | | | | 345 | | | | | 350 | | |
| Thr | Asp | Gly | Ser | Asn | Val | Val | Ala | Ala | Ser | Glu | Pro | Leu | Ala | Val | Leu |
| | | 355 | | | | | 360 | | | | | 365 | | | |
| Val | Asn | Lys | Gly | Thr | Ala | Ser | Ala | Ser | Glu | Ile | Leu | Ala | Gly | Ala | Leu |
| | 370 | | | | | 375 | | | | | 380 | | | | |
| Lys | Asp | Asn | Lys | Arg | Ala | Gln | Leu | Phe | Gly | Glu | Pro | Thr | Tyr | Gly | Lys |
| 385 | | | | | 390 | | | | | 395 | | | | | 400 |
| Gly | Lys | Ile | Gln | Ser | Val | Phe | Gln | Leu | Ser | Asp | Gly | Ser | Gly | Leu | Ala |
| | | | | 405 | | | | | 410 | | | | | 415 | |
| Val | Thr | Val | Ala | Arg | Tyr | Glu | Thr | Pro | Ala | His | Asn | Asp | Ile | Asp | Lys |
| | | | 420 | | | | | 425 | | | | | 430 | | |
| Val | Gly | Val | Ile | Pro | Asp | His | Pro | Leu | Pro | Ala | Ser | Phe | Pro | Lys | Asp |
| | | 435 | | | | | 440 | | | | | 445 | | | |
| Asp | Glu | Ser | Phe | Cys | Asn | Cys | Leu | Leu | Asn | Pro | Ala | Ser | Ala | Cys | His |
| | 450 | | | | | 455 | | | | | 460 | | | | |
| Leu | Asn | Arg | Val | Glu | Leu | Phe | Ser | Lys | | | | | | | |
| 465 | | | | | 470 | | | | | | | | | | |

( 2 ) INFORMATION FOR SEQ ID NO:16:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

```
CAGCCATGGC GCTCACGGAG GAGAAC                                              26
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
ATACTTGGGA TCCATATCAC G                                                   21
```

( 2 ) INFORMATION FOR SEQ ID NO:18:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:18:

```
Glu Val Met His Glu Arg Asn Ala His Asn Phe Pro Leu Asp Leu Ala
1               5                   1 0                  1 5
```

( 2 ) INFORMATION FOR SEQ ID NO:19:

( i ) SEQUENCE CHARACTERISTICS:
        ( A ) LENGTH: 1864 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: SPINACH D1 PROTEASE GENE ( x i ) SEQUENCE DESCRIPTION: SEQ ID NO:19:

```
GTTTCAATGG AGGTTATCTC GCGCCTCACC TTTGCTTCCG TTTCTTATCC CTTCATTTCT         60

TCCAACCTTA ATCCAACACC CATGCTCAAT TCTTTCAATT TCAGGGTGCT TTCCTGGAAC        120

AGTGCCCCCA CAAATGTTGC AGAAGCTCAT CTCCACCGCC TTTTACTGAG GAAATTGAAT        180

CCTGCTAATG ATCGGGTTGT TGGGATCTCT AACTTTGGTT GTTCATGCCG GTTAGATCTT        240

TGGCCAAGTT GGAGACGTCA TAAGAGGTTA TTTTTCCAGA ATGGTGTATC TACAATAAGG        300

TGGGAGGTCA AGAAGTGCAG TCCCAAATTT TATAAGATAG TCAGCAACTA TGAAAAATGC        360

AAACGTCATA TCTATGTCCC CTTTGTTCGT TTGGTTGTTG GAGTTGTATT GCTTATGTCT        420

GTTTCCGTAG CTTTAAACCA GGGCCCATCT TGGTCCCTTT CTGAGGAGAA TCGAATTTTC        480

CTAGAAGCGT GGAGAACAAT AGATCGTGCT TATGTTGACA AAACTTTTAA TGGACAAAGT        540

TGGTTTCGCT ATAGGGAGAA TGCACTGCGC AATGAGCCGA TGAACAGCAG AGAAGAGACA        600
```

```
TATACCGCAA  TAAGAAAGAT  GGTTGCTACA  CTGAATGATC  CATTCACTCG  TTTTCTGGAA    660

CCCGAAAAAT  TAAAGAGTTT  GCGGTCTGGA  ACTCAGAGTT  CGCTTACGGG  TGTAGGGATA    720

TCTATTGGCC  CCACCGCCGT  TGACCAATCA  TCCACTGGAT  TAGTTGTAAT  CTCAGCTACT    780

CCTGGGGCTC  CTGCCAGTAG  GGCCGGCATC  TTGCCTGGTG  ATGTAATATT  GGCAATTGAT    840

GATGCAAGTA  CTGACAAAAT  GGGCATATAT  GAGGCAGCAA  ATATCTTACA  GGGACCTGAT    900

GGAAGTTCTG  TTGATTTGAC  TATTTGCAGC  AGGGATGAGA  TAAAACATGT  GGTGCTGAAG    960

CGTGAGAGAA  TAACTCTAAG  CCCAGTAAAA  TCCAGATTAT  GTGAGATGCC  TGGTTCAGCA   1020

AAGGATGCTC  CTCCAAAAGT  TGGATATATC  AAGTTAACAT  CGTTCACTGA  GAATGCTTCT   1080

GATGCAGTAA  AGGAAGCTAT  AGAGACACTT  AGAAGTAACA  ATGTTAATGC  TTTTGTGCTG   1140

GACCTTCGAG  ATAATAGCGG  TGGTCTCTTT  CCAGAGGGAA  TCGAGATAGC  CAAAATTTGG   1200

TTGAACAAAG  GAGTTATTGT  ATATATATGT  GATAGTCGTG  GTGTTCGTGA  TATATATGAT   1260

GTTGAAGGGA  GCAGTGCTGT  AGCTGGTTCA  GAACCTCTTG  TTGTTCTGGT  GAACAAGGGA   1320

ACTGCAAGTG  CTAGTGAAAT  ATTAGCTGGG  GCATTAAAGG  ACAACAAACG  AGCAGTGGTA   1380

TTTGGAGAGC  CCACATATGG  AAAGGGCAAG  ATACAGTCAG  TTTTCGAGCT  ATCTGATGGA   1440

TCTGGCTTAG  CAGTCACAGT  TGCTCGCTAT  GAGACTCCTG  CTCACACAGA  TATTGACAAG   1500

GTGGGAATCA  AACCAGATCA  TCCTCTCCCA  GCATCTTTTC  CAAAGGATGA  AAATGATTTC   1560

TGCACCTGCG  TCCAAGATCC  ATCGTCTACT  TGTTATCTCA  ACGGCGTACA  ACTCTTTTCA   1620

AGATGACTAT  GGAAATGAAT  TTCTTCGGTG  TTTTCCATTT  GCGTTGCAAA  TTTTGGTTCT   1680

TTTAAAATTA  CTATTTTTTC  AGGATGCTAG  CCATCTCTGT  TGTAAGTTTG  TAACATCATT   1740

GGTTCCTTGT  ATATCTCTTC  ATCATCGTTC  CAACATCATA  GATTCTTTGT  ATATCTCTTT   1800

ATCGTCGTTC  GCGAAATTCA  GCATGGATTA  TCTTTTATCA  AACAATCTAA  CTTTGAGTAA   1860

ATCT                                                                    1864
```

( 2 ) INFORMATION FOR SEQ ID NO:20:

( i ) SEQUENCE CHARACTERISTICS:
        ( A ) LENGTH: 539 amino acids
        ( B ) TYPE: amino acid
        ( C ) STRANDEDNESS: unknown
        ( D ) TOPOLOGY: unknown ( i i ) MOLECULE TYPE: protein ( v i ) ORIGINAL SOURCE:
        ( B ) STRAIN: SPINACH D1 PROTEASE PROTEIN ( x i ) SEQUENCE DESCRIPTION: SEQ ID NO:20:

```
Met  Glu  Val  Ile  Ser  Arg  Leu  Thr  Phe  Ala  Ser  Val  Ser  Tyr  Pro  Phe
1                 5                        10                       15

Ile  Ser  Ser  Asn  Leu  Asn  Pro  Thr  Pro  Met  Leu  Asn  Ser  Phe  Asn  Phe
                 20                       25                       30

Arg  Val  Leu  Ser  Trp  Asn  Ser  Ala  Pro  Thr  Asn  Val  Ala  Glu  Ala  His
              35                       40                       45

Leu  His  Arg  Leu  Leu  Leu  Arg  Lys  Leu  Asn  Pro  Ala  Asn  Asp  Arg  Val
         50                       55                       60

Val  Gly  Ile  Ser  Asn  Phe  Gly  Cys  Ser  Cys  Arg  Leu  Asp  Leu  Trp  Pro
65                       70                       75                       80

Ser  Trp  Arg  Arg  His  Lys  Arg  Leu  Phe  Phe  Gln  Asn  Gly  Val  Ser  Thr
                   85                       90                       95

Ile  Arg  Trp  Glu  Val  Lys  Lys  Cys  Ser  Pro  Lys  Phe  Tyr  Lys  Ile  Val
                  100                      105                      110
```

| Ser | Asn | Tyr | Glu | Lys | Cys | Lys | Arg | His | Ile | Tyr | Val | Pro | Phe | Val | Arg |
|---|---|---|---|---|---|---|---|---|---|---|---|---|---|---|---|
| | | 115 | | | | 120 | | | | | 125 | | | | |
| Leu | Val | Val | Gly | Val | Val | Leu | Leu | Met | Ser | Val | Ser | Val | Ala | Leu | Asn |
| | 130 | | | | | 135 | | | | | 140 | | | | |
| Gln | Gly | Pro | Ser | Trp | Ser | Leu | Ser | Glu | Glu | Asn | Arg | Ile | Phe | Leu | Glu |
| 145 | | | | | 150 | | | | | 155 | | | | | 160 |
| Ala | Trp | Arg | Thr | Ile | Asp | Arg | Ala | Tyr | Val | Asp | Lys | Thr | Phe | Asn | Gly |
| | | | | 165 | | | | 170 | | | | | | 175 | |
| Gln | Ser | Trp | Phe | Arg | Tyr | Arg | Glu | Asn | Ala | Leu | Arg | Asn | Glu | Pro | Met |
| | | | 180 | | | | | 185 | | | | | 190 | | |
| Asn | Ser | Arg | Glu | Glu | Thr | Tyr | Thr | Ala | Ile | Arg | Lys | Met | Val | Ala | Thr |
| | | 195 | | | | | 200 | | | | | 205 | | | |
| Leu | Asn | Asp | Pro | Phe | Thr | Arg | Phe | Leu | Glu | Pro | Glu | Lys | Leu | Lys | Ser |
| | 210 | | | | | 215 | | | | | 220 | | | | |
| Leu | Arg | Ser | Gly | Thr | Gln | Ser | Ser | Leu | Thr | Gly | Val | Gly | Ile | Ser | Ile |
| 225 | | | | | 230 | | | | | 235 | | | | | 240 |
| Gly | Pro | Thr | Ala | Val | Asp | Gln | Ser | Ser | Thr | Gly | Leu | Val | Val | Ile | Ser |
| | | | | 245 | | | | | 250 | | | | | 255 | |
| Ala | Thr | Pro | Gly | Ala | Pro | Ala | Ser | Arg | Ala | Gly | Ile | Leu | Pro | Gly | Asp |
| | | | 260 | | | | | 265 | | | | | 270 | | |
| Val | Ile | Leu | Ala | Ile | Asp | Asp | Ala | Ser | Thr | Asp | Lys | Met | Gly | Ile | Tyr |
| | | 275 | | | | | 280 | | | | | 285 | | | |
| Glu | Ala | Ala | Asn | Ile | Leu | Gln | Gly | Pro | Asp | Gly | Ser | Ser | Val | Asp | Leu |
| | 290 | | | | | 295 | | | | | 300 | | | | |
| Thr | Ile | Cys | Ser | Arg | Asp | Glu | Ile | Lys | His | Val | Val | Leu | Lys | Arg | Glu |
| 305 | | | | | 310 | | | | | 315 | | | | | 320 |
| Arg | Ile | Thr | Leu | Ser | Pro | Val | Lys | Ser | Arg | Leu | Cys | Glu | Met | Pro | Gly |
| | | | | 325 | | | | | 330 | | | | | 335 | |
| Ser | Ala | Lys | Asp | Ala | Pro | Pro | Lys | Val | Gly | Tyr | Ile | Lys | Leu | Thr | Ser |
| | | | 340 | | | | | 345 | | | | | 350 | | |
| Phe | Thr | Glu | Asn | Ala | Ser | Asp | Ala | Val | Lys | Glu | Ala | Ile | Glu | Thr | Leu |
| | | 355 | | | | | 360 | | | | | 365 | | | |
| Arg | Ser | Asn | Asn | Val | Asn | Ala | Phe | Val | Leu | Asp | Leu | Arg | Asp | Asn | Ser |
| | 370 | | | | | 375 | | | | | 380 | | | | |
| Gly | Gly | Leu | Phe | Pro | Glu | Gly | Ile | Glu | Ile | Ala | Lys | Ile | Trp | Leu | Asn |
| 385 | | | | | 390 | | | | | 395 | | | | | 400 |
| Lys | Gly | Val | Ile | Val | Tyr | Ile | Cys | Asp | Ser | Arg | Gly | Val | Arg | Asp | Ile |
| | | | | 405 | | | | | 410 | | | | | 415 | |
| Tyr | Asp | Val | Glu | Gly | Ser | Ser | Ala | Val | Ala | Gly | Ser | Glu | Pro | Leu | Val |
| | | | 420 | | | | | 425 | | | | | 430 | | |
| Val | Leu | Val | Asn | Lys | Gly | Thr | Ala | Ser | Ala | Ser | Glu | Ile | Leu | Ala | Gly |
| | | 435 | | | | | 440 | | | | | 445 | | | |
| Ala | Leu | Lys | Asp | Asn | Lys | Arg | Ala | Val | Val | Phe | Gly | Glu | Pro | Thr | Tyr |
| | 450 | | | | | 455 | | | | | 460 | | | | |
| Gly | Lys | Gly | Lys | Ile | Gln | Ser | Val | Phe | Glu | Leu | Ser | Asp | Gly | Ser | Gly |
| 465 | | | | | 470 | | | | | 475 | | | | | 480 |
| Leu | Ala | Val | Thr | Val | Ala | Arg | Tyr | Glu | Thr | Pro | Ala | His | Thr | Asp | Ile |
| | | | | 485 | | | | | 490 | | | | | 495 | |
| Asp | Lys | Val | Gly | Ile | Lys | Pro | Asp | His | Pro | Leu | Pro | Ala | Ser | Phe | Pro |
| | | | 500 | | | | | 505 | | | | | 510 | | |
| Lys | Asp | Glu | Asn | Asp | Phe | Cys | Thr | Cys | Val | Gln | Asp | Pro | Ser | Ser | Thr |
| | | | 515 | | | | | 520 | | | | | 525 | | |
| Cys | Tyr | Leu | Asn | Gly | Val | Gln | Leu | Phe | Ser | Arg | | | | | |
| | 530 | | | | | 535 | | | | | | | | | |

( 2 ) INFORMATION FOR SEQ ID NO:21:

( i ) SEQUENCE CHARACTERISTICS:
        ( A ) LENGTH: 128 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:21:

```
Gly Thr Ala Gly Ser Val Thr Gly Val Gly Leu Glu Ile Thr Tyr Asp
 1               5                  10                   15
Gly Gly Ser Gly Gly Leu Ser Leu Tyr Asp Val Ser Asp Leu Leu Gln
            20                  25                  30
Gly Glu Ala Asp Ser Gln Val Glu Val Val Leu His Ala Pro Gly Ala
        35                  40                  45
Pro Ser Asn Thr Arg Leu Ala Thr Phe Asn Ser Asn Thr Thr Ala Ala
    50                  55                  60
Ala Gln Gln Ala Phe Thr Glu Leu Ser Asp Ile Tyr Ser Ala Asp Gly
65                  70                  75                  80
Asn Ser Ile Asp Ser Ala Thr Pro Leu Val Val Leu Val Asn Arg Leu
                85                  90                  95
Ile Gln Thr Val Val Asp Leu Ser Asp Ile Gly Val Ser Pro Asp Val
                100                 105                 110
Gln Leu Asp Pro Glu Val Leu Pro Thr Asp Leu Glu Gly Val Cys Arg
            115                 120                 125
```

( 2 ) INFORMATION FOR SEQ ID NO:22:

( i ) SEQUENCE CHARACTERISTICS:
        ( A ) LENGTH: 464 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:22:

```
Met His Ser Arg Thr Asn Cys Leu Gln Thr Ser Val Arg Ala Pro Gln
 1               5                  10                  15
Pro His Phe Arg Pro Phe Thr Ala Val Lys Thr Cys Arg Gln Arg Cys
            20                  25                  30
Ser Thr Thr Ala Ala Ala Ala Lys Arg Asp Gln Ala Gln Glu Gln Gln
        35                  40                  45
Pro Trp Ile Gln Val Gly Leu Gly Leu Ala Ala Ala Ala Thr Ala Val
    50                  55                  60
Ala Val Gly Leu Gly Ala Ala Ala Leu Pro Ala Gln Ala Val Thr Ser
65                  70                  75                  80
Glu Gln Leu Leu Phe Leu Glu Ala Trp Arg Ala Val Asp Arg Ala Tyr
                85                  90                  95
Val Asp Lys Ser Phe Asn Gly Gln Ser Trp Phe Lys Leu Arg Glu Thr
                100                 105                 110
Tyr Leu Lys Arg Glu Pro Met Asp Arg Arg Ala Gln Thr Tyr Asp Ala
            115                 120                 125
Ile Arg Lys Leu Leu Ala Val Leu Asp Asp Pro Phe Thr Arg Phe Leu
        130                 135                 140
Glu Pro Ser Arg Leu Ala Ala Leu Arg Arg Gly Thr Ala Gly Ser Val
```

| | | | | 145 | | | | 150 | | | | 155 | | | 160 |
|---|---|---|---|---|---|---|---|---|---|---|---|---|---|---|---|
| Thr | Gly | Val | Gly | Leu | Glu | Ile | Thr | Tyr | Asp | Gly | Gly | Ser | Gly | Arg | Asp |
| | | | | 165 | | | | 170 | | | | | | 175 | |
| Val | Val | Val | Leu | Thr | Pro | Ala | Pro | Gly | Gly | Pro | Ala | Glu | Arg | Ala | Gly |
| | | | 180 | | | | | 185 | | | | | 190 | | |
| Ala | Arg | Ala | Gly | Asp | Val | Ile | Val | Thr | Val | Asp | Gly | Thr | Ala | Val | Lys |
| | | 195 | | | | | 200 | | | | | 205 | | | |
| Gly | Leu | Ser | Leu | Tyr | Asp | Val | Ser | Asp | Leu | Leu | Gln | Gly | Glu | Ala | Asp |
| | 210 | | | | | 215 | | | | | 220 | | | | |
| Ser | Gln | Val | Glu | Val | Leu | His | Ala | Pro | Gly | Ala | Pro | Ser | Asn | Thr |
| 225 | | | | | 230 | | | | | 235 | | | | | 240 |
| Arg | Thr | Leu | Gln | Leu | Thr | Arg | Gln | Lys | Val | Thr | Ile | Asn | Pro | Val | Thr |
| | | | | 245 | | | | | 250 | | | | | 255 | |
| Phe | Thr | Thr | Cys | Ser | Asn | Val | Ala | Ala | Ala | Ala | Leu | Pro | Pro | Gly | Ala |
| | | | 260 | | | | | 265 | | | | | 270 | | |
| Ala | Arg | Gln | Gln | Leu | Gly | Tyr | Val | Arg | Leu | Ala | Thr | Phe | Asn | Ser | Asn |
| | | 275 | | | | | 280 | | | | | 285 | | | |
| Thr | Thr | Ala | Ala | Ala | Gln | Gln | Ala | Phe | Thr | Glu | Leu | Ser | Lys | Gln | Gly |
| 290 | | | | | 295 | | | | | 300 | | | | | |
| Val | Ala | Gly | Leu | Val | Leu | Asp | Ile | Arg | Asn | Asn | Gly | Gly | Gly | Leu | Phe |
| 305 | | | | | 310 | | | | | 315 | | | | | 320 |
| Pro | Ala | Gly | Val | Asn | Val | Ala | Arg | Met | Leu | Val | Asp | Arg | Gly | Asp | Leu |
| | | | | 325 | | | | | 330 | | | | | 335 | |
| Val | Leu | Ile | Ala | Asp | Ser | Gln | Gly | Ile | Arg | Asp | Ile | Tyr | Ser | Ala | Asp |
| | | | 340 | | | | | 345 | | | | | 350 | | |
| Gly | Asn | Ser | Ile | Asp | Ser | Ala | Thr | Pro | Leu | Val | Val | Leu | Val | Asn | Arg |
| | | 355 | | | | | 360 | | | | | 365 | | | |
| Gly | Thr | Ala | Ser | Ala | Ser | Glu | Val | Leu | Ala | Gly | Ala | Leu | Arg | Asp | Ser |
| | 370 | | | | | 375 | | | | | 380 | | | | |
| Lys | Arg | Gly | Leu | Ile | Ala | Gly | Glu | Arg | Thr | Phe | Gly | Lys | Gly | Leu | Ile |
| 385 | | | | | 390 | | | | | 395 | | | | | 400 |
| Gln | Thr | Val | Val | Asp | Leu | Ser | Asp | Gly | Ser | Gly | Val | Ala | Val | Thr | Val |
| | | | | 405 | | | | | 410 | | | | | 415 | |
| Ala | Arg | Tyr | Gln | Thr | Pro | Ala | Gly | Val | Asp | Ile | Asn | Lys | Ile | Gly | Val |
| | | | 420 | | | | | 425 | | | | | 430 | | |
| Ser | Pro | Asp | Val | Gln | Leu | Asp | Pro | Glu | Val | Leu | Pro | Thr | Asp | Leu | Glu |
| | | 435 | | | | | 440 | | | | | 445 | | | |
| Gly | Val | Cys | Arg | Val | Leu | Gly | Ser | Asp | Ala | Ala | Pro | Arg | Leu | Phe | Gly |
| | 450 | | | | | 455 | | | | | 460 | | | | |

( 2 ) INFORMATION FOR SEQ ID NO:23:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

CTGAAGGACA GCAAGCGGGG CCTCATAGCT GGCGAGCGCA CCTTTGGCAA GGGCCTCATT    60

( 2 ) INFORMATION FOR SEQ ID NO:24:

( i ) SEQUENCE CHARACTERISTICS:
( A ) LENGTH: 20 amino acids
( B ) TYPE: amino acid (C) STRANDEDNESS: unknown
(D) TOPOLOGY: unknown (ii) MOLECULE TYPE: peptide (xi) SEQUENCE DESCRIPTION: SEQ ID NO:24:

```
Leu Lys Asp Ser Lys Arg Gly Leu Ile Ala Gly Glx Arg Thr Phe Gly
1               5                   10                  15
Lys Gly Leu Ile
            20
```

(2) INFORMATION FOR SEQ ID NO:25:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
CTCAAGGACA GCAAGCGGGC CTCATAGCTG GCGAGCGCAC CTTTGGCAAG GGCCTCATT    59
```

(2) INFORMATION FOR SEQ ID NO:26:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:26:

```
Leu Lys Asp Ser Lys Arg Ala Ser
1               5
```

(2) INFORMATION FOR SEQ ID NO:27:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
CTCAAGCACA GCAAGCGGGC CTCATTAGCT GGCGAGCGCA CCTTTGGCAA GGGCCTCATT    60
```

(2) INFORMATION FOR SEQ ID NO:28:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:28:

```
Leu Lys Asp Ser Lys Arg Ala Ser Leu Ala Gly Glx Arg Thr Phe Gly
1               5                   10                  15
Lys Gly Leu Ile
            20
```

(2) INFORMATION FOR SEQ ID NO:29:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:29:

GCCCGATCGC CTCATA                              16